United States Patent
Stricker-Kongra et al.

(10) Patent No.: US 6,537,765 B2
(45) Date of Patent: *Mar. 25, 2003

(54) GPR10 AS A TARGET FOR IDENTIFYING WEIGHT MODULATING COMPOUNDS

(75) Inventors: Alain Stricker-Kongra, Watertown, MA (US); Wei Gu, Brookline, MA (US)

(73) Assignee: Millennium Pharmaceuticals, Inc., Cambridge, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 09/799,955

(22) Filed: Mar. 6, 2001

(65) Prior Publication Data

US 2001/0010921 A1 Aug. 2, 2001

Related U.S. Application Data

(63) Continuation of application No. 09/172,353, filed on Oct. 14, 1998, now Pat. No. 6,197,530.
(60) Provisional application No. 60/101,380, filed on Sep. 22, 1998.

(51) Int. Cl.[7] .................. G01N 33/53; G01N 33/566; G01N 33/567; C12N 5/22; C12N 5/18
(52) U.S. Cl. ................. 435/7.21; 435/29; 435/325; 435/326; 435/252.3; 435/254.11; 435/320.1; 435/7.2; 435/334; 436/501; 436/503
(58) Field of Search ..................... 435/7.2, 29, 325, 435/326, 252.3, 254.11, 320.1, 7.21, 334; 436/501, 503

(56) References Cited

FOREIGN PATENT DOCUMENTS

| EP | 0 845 529 A2 | 6/1998 |
|---|---|---|
| WO | WO 97/08317 | 3/1997 |

OTHER PUBLICATIONS

Hinuma et al., "A prolactin–releasing peptide in the brain" Nature 393:195–290, May 21, 1998.
Marchese et al., "Cloning and chromosomal mapping of three novel genes, GPR9, GPR10, and GPR14 . ." Genomics 29:335–344, 1995.
Welch et al., "Sequence and tissue distribution of a canidate G–coupled receptor cloaned from . . . " Biochem. and Biophys. Res. Comm. 209(2):606–613, 1995.
GenBank Accession No. 1346167; Merchese et al. 1995.
GenBank Accession No. 2495035, Welch, 1995.
GenBank Accession No. 3273225, Hinum, 1998.

*Primary Examiner*—Gary Kunz
*Assistant Examiner*—Fozia Hamud
(74) *Attorney, Agent, or Firm*—Millennium Pharmaceuticals, Inc.

(57) ABSTRACT

Assays for the identification of compounds useful for the modulation of body weight, metabolic rate, or feeding behavior are disclosed. Such compounds are useful for the treatment body weight disorders, e.g., obesity and cachexia. The methods involve cell-free and cell-based assays that identify compounds which alter ligand binding to and/or alter the activity of GPR10, a G protein-coupled receptor, optionally followed by an in vivo assay of the effect of the compound on feeding behavior, body weight, or metabolic rate.

16 Claims, 8 Drawing Sheets

ATGACCTCACTGTCCACTGAGACCACTGGAGACCCCGATTTGTCTTCTGG

GCTGTTGCCAGCCAGCTCCACTCCAGCCAACCAGAGCGCAGAGGCCTCG

GAGGGCAACCTGTCTGCGACGGTTCCCCGAGCTGCAGCAGTCACGCCGTT

CCAGAGCCTGCAGCTGGTGCACCAGCTGAAGGGGTTGATCGTGATGCTGT

ACAGCATTGTGGTGGTCGTGGGTCTGGTGGGCAACTGCCTGCTTGTGCTG

GTGATCGCGCGCGTGCGCCGGCTGCACAACGTGACCAACTTCCTCATTGG

CAACCTGGCCTTGTCCGACGTGCTCATGTGTGCCGCCTGTGTGCCTCTCAC

GCTGGCTTATGCCTTTGAACCTCGGGGCTGGGTGTTCGGTGGAGGCCTGT

GTCATCTGGTTTTCTTCCTGCAGCCGGTCACCGTCTATGTATCGGTGTTCA

CACTCACCACAATCGCCTTGGACCGCTATGTGGTTCTGGTGCACCCGCTA

CGTCGGCGCATTTCACTGAGGCTCAGCGCCTACGCGGTGCTGGGCATCTG

GGCTCTATCTGCAGTGCTGGCGCTGCCGGCCGCGGTGCACACCTACCATG

TGGAGCTCAAGCCCCACGACGTGCGCCTCTGCGAGGAGTTCTGGGGCTC

GCAGGAGCGCCAACGCCAGATCTACGCCTGGGGGCTGCTTCTGGGCACC

TATTTGCTCCCCCTGCTGGCCATCCTCCTGTCTTACGTACGGGTGTCAGTG

AAGCTGAGGAACCGCGTGGTGCCTGGCAGCGTGACCCAGAGTCAAGCTG

ACTGGGACCGAGCGCGTCGCCGCCGCACTTTCTGTCTGCTGGTGGTGGTG

GTGGTAGTGTTCGCGGTCTGCTGGCTGCCGCTGCACATTTTCAACCTATTG

CGAGACCTGGACCCGCGTGCCATCGACCCCTACGCCTTCGGGCTGGTGC

AGCTACTCTGCCACTGGCTTGCTATGAGCTCCGCCTGCTACAACCCCTTCA

TCTATGCATGGCTGCACGACAGCTTTCGAGAGGAGCTGCGCAAGATGCTG

CTGTCCTGGCCCCGCAAGATTGTGCCTCATGGCCAGAACATGACCGTCAG

CGTGGTCATCTGA

FIG. 1

MTSLSTETTGDPDLSSGLLPASSTPANQSAEASEGNLSATVPRAA

AVTPFQSLQLVHQLKGLIVMLYSIVVVVGLVGNCLLVLVIARVRRL

HNVTNFLIGNLALSDVLMCAACVPLTLAYAFEPRGWVFGGGLCHL

VFFLQPVTVYVSVFTLTTIALDRYVVLVHPLRRRISLRLSAYAVLGI

WALSAVLALPAAVHTYHVELKPHDVRLCEEFWGSQERQRQIYAW

GLLLGTYLLPLLAILLSYVRVSVKLRNRVVPGSVTQSQADWDRAR

RRRTFCLLVVVVVVFAVCWLPLHIFNLLRDLDPRAIDPYAFGLVQL

LCHWLAMSSACYNPFIYAWLHDSFREELRKMLLSWPRKIVPHGQ

NMTVSVVI*

FIG. 2

```
              1                                                                          80
hGR3  (human) MASSTTRGPRVSDLFSGLPPAVTTPANQSAEEASAGNGSVAGADAPAVTPFQSLQLVHQLKGLIVLLYSVVVVGLVGNCL
GPR10 (human) MASSTTRGPRVSDLFSGLPPAVTTPANQSAEEASAGNGSVAGADAPAVTPFQSLQLVHQLKGLIVLLYSVVVVGLVGNCL
UHR1  (rat)   MTSLPPGTTGDPDLFSGPSPAGSTPANQSAEEASESNVSATVPRAAAVTPFQSLQLVHQLKGLIVMLYSIVVVGLVGNCL
101   (mouse) MTSLSTETTGDPDLSSGLLPASSTPANQSAEEASEGNLSATVPRAAAVTPFQSLQLVHQLKGLIVMLYSIVVVGLVGNCL 81                                                                         160
hGR3  (human) LVLVIARVRRLHNVTNFLIGNLALSDVLMCTACVPLTLAYAFEPRGWVFGGGLCHLVFFLQPVTVYVSVFTLTTIAVDRY
GPR10 (human) LVLVIARVPRLHNVTNFLIGNLALSDVLMCTACVPLTLAYAFEPRGWVFGGGLCHLVFFLQPVTVYVSVFTLTTIAVDRY
UHR1  (rat)   LVLVIARVRRLHNVTNFLIGNLALSDVLMCAACVPLTLAYAFEPRGWVFGGGLCHLVFFLQPVTVYVSVFTLTTIAVDRY
101   (mouse) LVLVIARVRRLHNVTNFLIGNLALSDVLMCAACVPLTLAYAFEPRGWVFGGGLCHLVFFLQPVTVYVSVFTLTTIALDRY 161                                                                        240
hGR3  (human) VVLVHPLRRRISLRLSAYAVLAIWALSAVLALPAAVHTYHVELKPHDVRLCEEFWGSQERQRQLYAWGLLLVTYLLPLIV
GPR10 (human) VVLVHPLRR-ASRCASAYAVLAIWALSAVLALPPAVHTYHVELKPHDVRLCEEFWGSQERQRQLYAWGLLLVTYLLPLIV
UHR1  (rat)   VVLVHPLRRRISIKLSAYAVLGIWALSAVLALPAAVHTYHVELKPHDVRLCEEFWGSQERQRQIYAWGLLLGTYLLPLLA
101   (mouse) VVLVHPLRRRISLKLSAYAVLGIWALSAVLALPAAVHTYHVELKPHDVRLCEEFWGSQERQRQIYAWGLLLGTYLLPLLA 241                                                                        320
hGR3  (human) ILLSYVRVSVKLRNRVVPGCVTQSQADWDRARRRRTFCLLVVVVVFAVCWLPLHVFNLLRDLDPHAIDPYAFGLVQLLC
GPR10 (human) ILLSYVRVSVKLRNRVVPGCVTQSQADWDRARRRRTFCLLVVVVVFAVCWLPLHVFNLLRDLDPHAIDPYAFGLVQLLC
UHR1  (rat)   ILLSYVRVSVKLRNRVVPGSVTQSQADWDRARRRRTFCLLVVVVVVFALCWLPLHIFNLLRDLDPRAIDPYAFGLVQLLC
101   (mouse) ILLSYVRVSVKLRNRVVPGSVTQSQADWDRARRRRTFCLLVVVVVVFAVCWLPLHIFNLLRDLDPRAIDPYAFGLVQLLC 321                                         400
hGR3  (human) HWLAMSSACYNPFIYAWLHDSFREELRKLLIVAWPRKIAPHGQNMTVSVVI
GPR10 (human) HWLAMSSACYNPFIYAWLHDSFREELRKLLIVAWPRKIAPHGQNMTVSVVI
UHR1  (rat)   HWLAMSSACYNPFIYAWLHDSFREELRKMLLSWPRKIVPHGQNMTVSVVI
101   (mouse) HWLAMSSACYNPFIYAWLHDSFREELRKMLLSWPRKIVPHGQNMTVSVVI
```

FIG. 8

GPR10 AS A TARGET FOR IDENTIFYING WEIGHT MODULATING COMPOUNDS

RELATED APPLICATION INFORMATION

This application is a continuation (and claims the benefit of priority under 35 USC 120) of U.S. application Ser. No. 09/172,353, U.S. Pat. No. 6,197,530 filed Oct. 4, 1998, which application claims the benefit of priority of U.S. application Ser. No. 60/101,380, filed Sep. 22, 1998. The disclosure of the prior applications are considered part of (and is incorporated by reference in) the disclosure of this application.

BACKGROUND OF THE INVENTION

The G-protein-coupled receptors (GPCR) form an important class of peptide-binding receptors. The various members of the GPCR family mediate a wide variety of intercellular signals.

Members of the GPCR family have seven helical domains which span the cell membrane and are linked by three extracellular loops and three intracellular loops. The receptors also posses an extracellular amino terminal tail and an intracellular carboxy terminal tail. The intracellular loops interact with a G-protein that can switch from a GDP-binding form to a GTP-binding form.

The binding of an appropriate ligand to a GPCR initiates the conversion of the coupled C-protein from its GDP-binding form to its GTP-binding form. This conversion, in turn, initiates a signal transduction cascade that generates a biological response. Depending on the nature of the GPCR, signal transduction activity can be measured by measuring the intracellular $Ca^{2+}$ level, phospholipase C activation, the inositol triphosphate ($IP_3$) level, the diacylglycerol level, or the adenosine cyclic 3', 5'-monophosphate (AMP) level.

Marchese et al. (*Genomics* 29:335, 1995) describes the cloning and chromosomal mapping of GPR10, a human GPCR. Marchese et al. analyzed GPR10 expression in the brain and reported that no human GPR10 expression was observed in hypothalamus, putamen, pons, hippocampus, frontal cortex, thalamus, and cerebellum.

Welch et al. (*Biochem. Biophys Res. Comm.* 209:606, 1995) describes the cloning of UHR-1, a rat GPCR, from the hypothalamic suprachiasmatic nucleic, the circadian pacemaker of the human brain. According to Welch et al., UHR-1 has sequence similarity at the amino acid level to the receptors for the tachykinins, substance P, and substance K; the somatostatin receptors SSTR5 and SSTR3; the neuropepticle Y1 receptor; the delta, kappa, and mu opioid receptors, and the gastrin-CCK-B receptor. According to Welch et al., rat UHR-1 is expressed in rat pituitary, cerebellum, hypothalamus, pons, and hippocampus. No expression is present in rat neonatal brain, adult rat liver, lung, pancreas, kidney, spleen, small intestine, adrenal gland, testes, thymus, aorta, heart, skeletal muscle, or diaphragm.

Duhl (PCT Publication No. WO 97/08317) describes a protein referred to as "human hypothalamic receptor" or "hHR". According to Duhl, hHR is a seven-transmembrane receptor. Duhl suggests that hHR can be used to identify agonists and antagonists of hHR activity.

Hinuma et al. (EP 0 845 529 A2) discloses two forms of a G-protein coupled receptor protein. Hinuma et al. report that one of the two forms of the disclosed G protein coupled receptor is expressed in the brain.

Hinuma et al. (Nature 393–272, 1998) describes "prolactin-releasing peptide" (PrRP) a peptide which binds to hGR3, a receptor that is expressed in human pituitary and is, according to Hinuma et al., nearly identical to both GPR10 and the human homologue of rat UHR-1. Hinuma et al. report that PrRP stimulates release of prolactin from anterior pituitary cells of lactating rats in vitro. Hinuma et al. also report that expression of PrRP and its receptor appear to fluctuate in the medulla oblongata and pituitary during pregnancy and lactation, respectively, in rats. Based on these results, Hinuma et al. suggest that the levels of PrRP and its receptor are closely related to the regulation of reproductive processes.

SUMMARY OF THE INVENTION

The invention features assays for the identification of compounds useful for the modulation of body weight. Such compounds are useful for the treatment of obesity and cachexia. The methods of the invention involve cell-free and cell-based assays that identify compounds (modulators) which bind to and/or activate or inhibit the activity of GPR10, a G protein-coupled receptor, followed by an in vivo assay of the effect of the compound on feeding behavior, body weight, or metabolic rate. The invention also features compounds which bind to and/or activate or inhibit the activity of GPR10 as well as pharmaceutical compositions comprising such compounds.

In addition, the invention includes nucleic acid molecules comprising a nucleotide sequence encoding all or a portion of murine GPR10, polypeptides comprising all or a portion of murine GPR10, antibodies directed against murine GPR10, and animals harboring a murine GPR10 transgene (e.g., mice overexpressing murine GPR10).

The invention also features pharmaceuticals compositions comprising a compound identified using the screening methods of the invention as a well as methods for preparing such compositions by combining a such a compound and a pharmaceutically acceptable carrier. Also within the invention are pharmaceutical compositions comprising a compound identified using the screening assays of the invention packaged with instructions for use. For modulators that are antagonists of GPR10 activity or expression, the instructions specify use of the pharmaceutical composition for treatment of high body weight (e.g., for reduction of body weight). For modulators that are agonists of GPR10 activity or expression, the instructions would specify use of the pharmaceutical composition for treatment of low body weight (i.e., for increase of body weight).

BRIEF DESCRIPTION OF THE DRAWINGS

FIG. 1 depicts the nucleic acid sequence of a cDNA encoding murine GPR10.

FIG. 2 depicts the predicted amino acid sequence of murine GPR10.

FIG. 8 depicts an alignment of human GPR10 with hGR3 (human), UHR1 (rat), and murine GPR10 (also referred to as 101).

DETAILED DESCRIPTION OF THE INVENTION

I. Screening Assays

Figure 3:
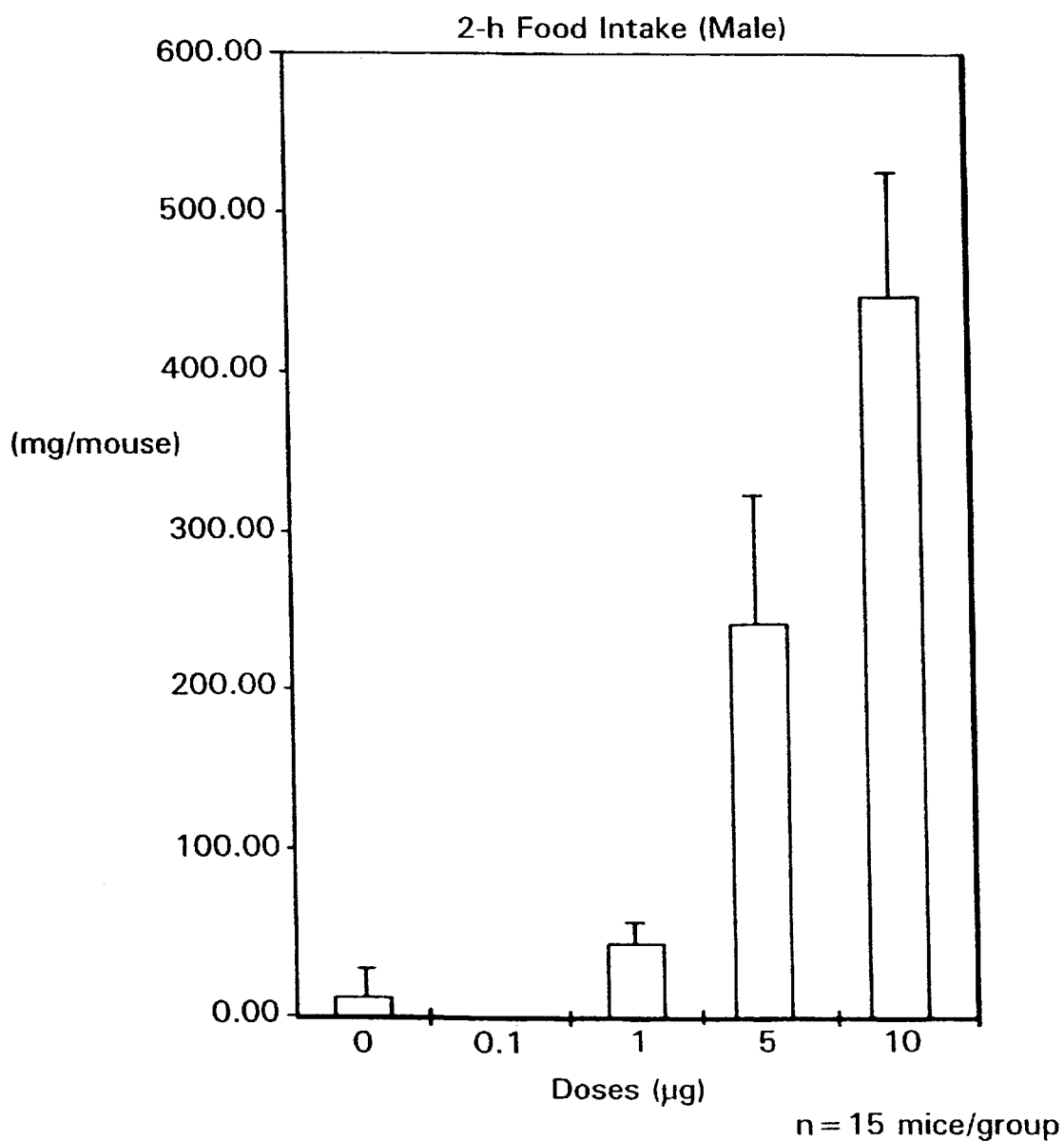
FIG. 3 is a graph illustrating the results of an experiment examining the effect of PrRP on the feeding behavior of lean male mice.

The invention provides methods (also referred to herein as a "screening assays") for identifying compounds which can be used for the modulation of body weight, e.g., for the treatment of a body weight disorder. The methods entail identifying candidate or test compounds or agents (e.g., peptides, peptidomimetics, small molecules or other drugs) which bind GPR10 and/or have a stimulatory or inhibitory effect on the activity or the expression of GPR10 and then determining which of the compounds that bind GPR10 or have a stimulatory or inhibitory effect on the activity or the expression of GPR10 have an effect on the feeding behavior, body weight, or metabolic rate of a mammal (e.g., a mouse or a rat) in an in vivo assay.

Candidate or test compounds or agents which bind GPR10 and/or have a stimulatory or inhibitory effect on the activity or the expression of GPR10 are identified in assays that employ either cells which express a form of GPR10 (cell-based assays) or isolated GPR10 (cell-free assays). The various assays can employ a variety of forms of GPR10 a(e.g., full-length GPR10, a biologically active fragment of GPR10, or a fusion protein which includes all or a portion of GPR10). Moreover, the GPR10 can be derived from any suitable mammalian species (e.g., human GPR10, rat GPR10 (also referred to a UHR-1), or murine GPR10. The assay can be a binding assay entailing direct or indirect measurement of the binding of a test compound or known GPR10 ligand to GPR10. The assay can also be an activity assay entailing direct or indirect measurement of the activity of GPR10. The assay can also be an expression assay entailing direct or indirect measurement of the expression of GPR10 (e.g., GPR10 encoding mRNA or GPR10 protein). The various screening assays are combined with an in vivo assay entailing measuring the effect of the test compound on the feeding behavior, body weight, or metabolic rate of a mammal (e.g., a mouse or a rat).

In one embodiment, the invention provides assays for screening candidate or test compounds which bind to or modulate the activity of a membrane-bound (cell surface expressed) form of GPR10. Such assays can employ full-length GPR10, a biologically active fragment of GPR10, or a fusion protein which includes all or a portion of GPR10. As described in greater detail below, the test compound can be obtained by any suitable means, e.g., from conventional compound libraries. Determining the ability of the test compound to bind to a membrane-bound form of GPR10 can be accomplished, for example, by coupling the test compound with a radioisotope or enzymatic label such that binding of the test compound to the GPR10-expressing cell can be measured by detecting the labeled compound in a complex. For example, the test compound can be labeled with $^{125}I$, $^{35}S$, $^{14}C$, or $^{3}H$, either directly or indirectly, and the radioisotope detected by direct counting of radioemmission or by scintillation counting. Alternatively, the test compound can be enzymatically labeled with, for example, horseradish peroxidase, alkaline phosphatase, or luciferase, and the enzymatic label detected by determination of conversion of an appropriate substrate to product.

In a competitive binding format, the assay comprises contacting a GPR10-expressing cell with a known compound which binds GPR10 (e.g., PrRP) to form an assay mixture, contacting the assay mixture with a test compound, and determining the ability of the test compound to interact with the GPR10-expressing cell, wherein determining the ability of the test compound to interact with the GPR10-expressing cell comprises determining the ability of the test compound to preferentially bind the GPR10-expressing cell as compared to the known compound.

In another embodiment, the assay is a cell-based assay comprising contacting a cell expressing a membrane-bound form of a GPR10 (e.g., full-length GPR10, a biologically active fragment of GPR10, or a fusion protein which includes all or a portion of GPR10) expressed on the cell surface with a test compound and determining the ability of the test compound to modulate (e.g., stimulate or inhibit) the activity of the membrane-bound form of GPR10. Determining the ability of the test compound to modulate the activity of the membrane-bound form of GPR10 can be accomplished by any method suitable for measuring the activity of GPR10, e.g., any method suitable for measuring the activity of a G-protein coupled receptor or other seven-transmembrane receptor (described in greater detail below). The activity of a seven-transmembrane receptor can be measured in a number of ways, not all of which are suitable for any given receptor. Among the measures of activity are: alteration in intracellular $Ca^{2+}$ concentration, activation of phospholipase C, alteration in intracellular inositol triphosphate ($IP_3$) concentration, alteration in intracellular diacylglycerol (DAG) concentration, and alteration in intracellular adenosine cyclic 3', 5'-monophosphate (cAMP) concentration.

Determining the ability of the test compound to modulate the activity of GPR10 can be accomplished, for example, by determining the ability of GPR10 to bind to or interact with a target molecule. The target molecule can be a molecule with which GPR10 binds or interacts with in nature, for example, a molecule on the surface of a cell which expresses GPR10, a molecule on the surface of a second cell, a molecule in the extracellular milieu, a molecule associated with the internal surface of a cell membrane or a cytoplasmic molecule. The target molecule can be a component of a signal transduction pathway which facilitates transduction of an extracellular signal (e.g., a signal generated by binding of a GPR10 ligand, e.g., PrRP, to GPR10) through the cell membrane and into the cell. The target molecule can be, for example, a second intracellular protein which has catalytic activity or a protein which facilitates the association of downstream signaling molecules with GPR10. A GPR10 ligand such as PrRP is one example of a GPR10 target molecule.

Determining the ability of a GPR10 polypeptide to bind to or interact with a target molecule can be accomplished by one of the methods described above for determining direct binding. In one embodiment, determining the ability of a polypeptide of the invention to bind to or interact with a target molecule can be accomplished by determining the activity of the target molecule. For example, the activity of the target molecule can be determined by detecting induction of a cellular second messenger of the target (e.g., intracellular $Ca^{2+}$, diacylglycerol, IP3, etc.), detecting catalytic/enzymatic activity of the target on an appropriate substrate, detecting the induction of a reporter gene (e.g., a regulatory element that is responsive to a polypeptide of the invention operably linked to a nucleic acid encoding a detectable marker, e.g., luciferase), or detecting a cellular response.

The present invention also includes cell-free assays. Such assays involve contacting a form of GPR10 (e.g., full-length GPR10, a biologically active fragment of GPR10, or a fusion protein comprising all or a portion of GPR10) with a test compound and determining the ability of the test compound to bind to the GPR10 polypeptide. Binding of the test compound to the GPR10 polypeptide can be determined either directly or indirectly as described above. In one embodiment, the assay includes contacting the GPR10 polypeptide with a known compound which binds the GPR10 polypeptide to form an assay mixture, contacting the assay mixture with a test compound, and determining the ability of the test compound to interact with the GPR10 polypeptide, wherein determining the ability of the test compound to interact with the GPR10 polypeptide comprises determining the ability of the test compound to preferentially bind to the GPR10 polypeptide as compared to the known compound.

The cell-free assays of the present invention are amenable to use of either a membrane-bound form of a GPR10 polypeptide or a soluble fragment thereof. In the case of cell-free assays comprising the membrane-bound form of the polypeptide, it may be desirable to utilize a solubilizing agent such that the membrane-bound form of the polypeptide is maintained in solution. Examples of such solubilizing agents include non-ionic detergents such as n-octylglucoside, n-dodecylglucoside, n-dodecylmaltoside, octanoyl-N-methylglucamide, decanoyl-N-methylglucamide, Triton X-100, Triton X-114, Thesit, Isotridecypoly(ethylene glycol ether)n, 3-[(3-cholamidopropyl)dimethylamminio]-1-propane sulfonate (CHAPS), 3-[(3-cholamidopropyl)dimethylamminio]-2-hydroxy-1-propane sulfonate (CHAPSO), or N-dodecyl=N,N-dimethyl-3-ammonio-1-propane sulfonate.

In various embodiments of the above assay methods of the present invention, it may be desirable to immobilize the GPR10 polypeptide (or a GPR10 target molecule) to facilitate separation of complexed from uncomplexed forms of one or both of the proteins, as well as to accommodate automation of the assay. Binding of a test compound to the GPR10 polypeptide, or interaction of the GPR10 polypeptide with a target molecule in the presence and absence of a candidate compound, can be accomplished in any vessel suitable for containing the reactants. Examples of such vessels include microtitre plates, test tubes, and microcentrifuge tubes. In one embodiment, a fusion protein can be provided which adds a domain that allows one or both of the proteins to be bound to a matrix. For example, glutathione-S-transferase fusion proteins or glutathione-S-transferase fusion proteins can be adsorbed onto glutathione sepharose beads (Sigma Chemical; St. Louis, Mo.) or glutathione derivatized microtitre plates, which are then combined with the test compound or the test compound and either the non-adsorbed target protein or GPR10 polypeptide, and the mixture incubated under conditions conducive to complex formation (e.g., at physiological conditions for salt and pH). Following incubation, the beads or microtitre plate wells are washed to remove any unbound components and complex formation is measured either directly or indirectly, For example, as described above. Alternatively, the complexes can be dissociated from the matrix, and the level of binding or activity of GPR10 polypeptide can be determined using standard techniques.

Other techniques for immobilizing proteins on matrices can also be used in the screening assays of the invention. For example, either the GPR10 polypeptide or its target molecule can be immobilized utilizing conjugation of biotin and streptavidin. Biotinylated polypeptide of the invention or target molecules can be prepared from biotin-NHS (N-hydroxy-succinimide) using techniques well known in the art (e.g., biotinylation kit, Pierce Chemicals; Rockford, Ill.), and immobilized in the wells of streptavidin-coated 96 well plates (Pierce Chemical). Alternatively, antibodies reactive with GPR10 or target molecules but which do not interfere with binding of the polypeptide of the invention to its target molecule can be derivatized to the wells of the plate, and unbound target or polypeptidede of the invention trapped in the wells by antibody conjugation. Methods for detecting such complexes, in addition to those described above for the GST-immobilized complexes, include immunodetection of complexes using antibodies reactive with GPR10 or target molecule, as well as enzyme-linked assays which rely on detecting an enzymatic activity associated with GPR10 or target molecule.

The screening assay can also involve monitoring the expression of GPR10. For example, modulators of expression of GPR10 can be identified in a method in which a cell is contacted with a candidate compound and the expression of GPR10 protein or mRNA in the cell is determined. The level of expression of GPR10 protein or mRNA the presence of the candidate compound is compared to the level of expression of GPR10 protein or mRNA in the absence of the candidate compound. The candidate compound can then be identified as a modulator of expression of GPR10 based on this comparison. For example, when expression of GPR10 protein or mRNA protein is greater (statistically significantly greater) in the presence of the candidate compound than in its absence, the candidate compound is identified as a stimulator of GPR10 protein or mRNA expression. Alternatively, when expression of GPR10 protein or mRNA is less (statistically significantly less) in the presence of the candidate compound than in its absence, the candidate compound is identified as an inhibitor of GPR10 protein or mRNA expression. The level of GPR10 protein or mRNA expression in the cells can be determined by methods described below.

II. Test Compounds

Suitable test compounds for use in the screening assays of the invention can be obtained from any suitable source, e.g., conventional compound libraries. The test compounds can also be obtained using any of the numerous approaches in combinatorial library methods known in the art, including: biological libraries; spatially addressable parallel solid phase or solution phase libraries; synthetic library methods requiring deconvolution; the "one-bead one-compound" library method; and synthetic library methods using affinity chromatography selection. The biological library approach is limited to peptide libraries, while the other four approaches are applicable to peptide, non-peptide oligomer or small molecule libraries of compounds (Lam (1997) *Anticancer Drug Des.* 12:145).

Examples of methods for the synthesis of molecular libraries can be found in the art, for example in: DeWitt et al. (1993) *Proc. Natl. Acad. Sci. USA* 90:6909; Erb et al. (1994) *Proc. Natl. Acad. Sci. USA* 91:11422; Zuckermann et al. (1994). *J. Med. Chem.* 37:2678; Cho et al. (1993) *Science* 261:1303; Carrell et al. (1994) *Angew. Chem. Int. Ed. Engl.* 33:2059; Carell et al. (1994) *Angew. Chem. Int. Ed. Engl.* 33:2061; and Gallop et al. (1994) *J. Med. Chem.* 37:1233.

Libraries of compounds may be presented in solution (e.g., Houghten (1992) *BioTechniques* 13:412–421), or on beads (Lam (1991) *Nature* 354:82–84), chips (Fodor (1993) *Nature* 364:555–556), bacteria (U.S. Pat. No. 5,223,409), spores (U.S. Pat. Nos. 5,571,698; 5,403,484; and 5,223, 409), plasmids (Cull et al. (1992) *Proc. Natl. Acad. Sci. USA* 89:1865–1869) or phage (Scott and Smith (1990) *Science* 249:386–390; Devlin (1990) *Science* 249:404–406; Cwirla et al. (1990) *Proc. Math. Acad. Sci. USA* 87:6378–6382; and Felici (1991) *J. Mol. Biol.* 222:301–310).

III. Modeling of Modulators

Computer modeling and searching technologies permit identification of compounds, or the improvement of already identified compounds, that can modulate GPR10 expression or activity. Having identified such a compound or composition, the active sites or regions are identified. Such active sites might typically be ligand binding sites, such as the interaction domain of PrRP with GPR10. The active site can be identified using methods known in the art including, for example, from the amino acid sequences of peptides, from the nucleotide sequences of nucleic acids, or from study of complexes of the relevant compound or composition with its natural ligand. In the latter case, chemical or X-ray crystallographic methods can be used to find the active site by finding where on the factor the complexed ligand is found.

Next, the three dimensional geometric structure of the active site is determined. This can be done by known methods, including X-ray crystallography, which can determine a complete molecular structure. On the other hand, solid or liquid phase NMR can be used to determine certain intramolecular distances. Any other experimental method of structure determination can be used to obtain partial or complete geometric structures. The geometric structures may be measured with a complexed ligand, natural or artificial, which may increase the accuracy of the active site structure determined.

If an incomplete or insufficiently accurate structure is determined, the methods of computer based numerical modeling can be used to complete the structure or improve its accuracy. Any recognized modeling method may be used, including parameterized models specific to particular biopolymers such as proteins or nucleic acids, molecular dynamics models based on computing molecular motions, statistical mechanics models based on thermal ensembles, or combined models. For most types of models, standard molecular force fields, representing the forces between constituent atoms and groups, are necessary, and can be selected from force fields known in physical chemistry. The incomplete or less accurate experimental structures can serve as constraints on the complete and more accurate structures computed by these modeling methods.

Finally, having determined the structure of the active site, either experimentally, by modeling, or by a combination, candidate modulating compounds can be identified by searching databases containing compounds along with information on their molecular structure. Such a search seeks compounds having structures that match the determined active site structure and that interact with the groups defining the active site. Such a search can be manual, but is preferably computer assisted. These compounds found from this search are potential GPR10 modulating compounds.

Alternatively, these methods can be used to identify improved modulating compounds from an already known modulating compound or ligand. The composition of the known compound can be modified and the structural effects of modification can be determined using the experimental and computer modeling methods described above applied to the new composition. The altered structure is then compared to the active site structure of the compound to determine if an improved fit or interaction results. In this manner systematic variations in composition, such as by varying side groups, can be quickly evaluated to obtain modified modulating compounds or ligands of improved specificity or activity.

Kaul (1998) *Prog. Drug Res.* 50:9–105 provides a review of modeling techniques for the design of receptor ligands and drugs. Computer programs that screen and graphically depict chemicals are available from companies such as BioDesign, Inc. (Pasadena, Calif.), Oxford Molecular Design (Oxford, UK), and Hypercube, Inc. (Cambridge, Ontario).

Although described above with reference to design and generation of compounds which could alter binding, one could also screen libraries of known compounds, including natural products or synthetic chemicals, and biologically active materials, including proteins, for compounds which are inhibitors or activators.

IV. Isolated Nucleic Acid Molecules

One aspect of the invention pertains to isolated nucleic acid molecules that encode murine GPR10 or a biologically active portion thereof, as well as nucleic acid molecules sufficient for use as hybridization probes to identify nucleic acid molecules encoding murine GPR10 and fragments of such nucleic acid molecules suitable for use as PCR primers for the amplification or mutation of nucleic acid molecules. As used herein, the term "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA. This section describes murine GPR10 nucleic acids and methods for making and using such nucleic acids. However, the same techniques can be employed to make and use human GPR10 nucleic acids.

An "isolated" nucleic acid molecule is one which is separated from other nucleic acid molecules which are present in the natural source of the nucleic acid molecule. Preferably, an "isolated" nucleic acid molecule is free of sequences (preferably protein encoding sequences) which naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb or 0.1 kb of nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material, or culture medium when produced by recombinant techniques, or substantially free of chemical precursors or other chemicals when chemically synthesized.

A nucleic acid molecule of the present invention, e.g., a nucleic acid molecule having the nucleotide sequence of SEQ ID NO:1 or 2, can be isolated using standard molecular biology techniques and the sequence information provided herein. Using all or a portion of the nucleic acid sequences of SEQ ID NO:1 or 2 as a hybridization probe, nucleic acid molecules of the invention can be isolated using standard hybridization and cloning techniques (e.g., as described in Sambrook et al., eds., *Molecular Cloning: A Laboratory Manual*, 2nd ed., Cold Spring Harbor Laboratory, Cold Spring Harbor Laboratory Press, Cold Spring Harbor, N.Y., 1989).

A nucleic acid molecule of the invention can be amplified using cDNA, mRNA or genomic DNA as a template and appropriate oligonucleotide primers according to standard PCR amplification techniques. The nucleic acid so amplified can be cloned into an appropriate vector and characterized by DNA sequence analysis. Furthermore, oligonucleotides corresponding to all or a portion of a nucleic acid molecule of the invention can be prepared by standard synthetic techniques, e.g., using an automated DNA synthesizer.

Moreover, a nucleic acid molecule of the invention can comprise only a portion of a nucleic acid sequence encoding murine GPR10, for example, a fragment which can be used as a probe or primer or a fragment encoding a biologically active portion of murine GPR10. The nucleotide sequence determined from the cloning one gene allows for the generation of probes and primers designed for use in identifying and/or cloning allelic variants and other variants of GPR10. The probe/primer typically comprises substantially purified oligonucleotide. The oligonucleotide typically comprises a region of nucleotide sequence that hybridizes under stringent conditions to at least about 12, preferably about 25, more preferably about 50, 75, 100, 125, 150, 175, 200, 250, 300, 350 or 400 consecutive nucleotides of the sense or antisense sequence of SEQ ID NO:1 or 2 of a naturally occurring mutant or allelic variant of SEQ NO:1 or 2.

Probes based on the sequence of a nucleic acid molecule of the invention can be used to detect transcripts or genomic sequences encoding the same protein molecule encoded by a selected nucleic acid molecule. The probe comprises a label group attached thereto, e.g., a radioisotope, a fluorescent compound, an enzyme, or an enzyme co-factor. Such probes can be used as part of a diagnostic test kit for identifying cells or tissues which mis-express the protein, such as by measuring levels of a nucleic acid molecule encoding the protein in a sample of cells from a subject, e.g., detecting mRNA levels or determining whether a gene encoding the protein has been mutated or deleted.

A nucleic acid fragment encoding a "biologically active portion" of murine GPR10 can be prepared by isolating a portion of SEQ ID NO:2 which encodes a polypeptide having a biological activity, expressing the encoded portion of the polypeptide protein (e.g., by recombinant expression in vitro) and assessing the activity of the encoded portion of the polypeptide.

The invention further encompasses nucleic acid molecules that differ from the nucleotide sequence of SEQ ID NO:1 or 2 due to degeneracy of the genetic code and thus encode the same protein as that encoded by the nucleotide sequence shown in SEQ ID NO:2.

In addition to the nucleotide sequence shown in SEQ ID NO:1, it will be appreciated by those skilled in the art that DNA sequence polymorphisms that lead to changes in the amino acid sequence may exist within a population. Such genetic polymorphisms may exist among individuals within a population due to natural allelic variation. An allele is one of a group of genes which occur alternatively at a given genetic locus. As used herein, the phrase "allelic variant" refers to a nucleotide sequence which occurs at a given locus or to a polypeptide encoded by the nucleotide sequence. Such natural allelic variations can typically result in 1–5% variance in the nucleotide sequence of a given gene. Alternative alleles can be identified by sequencing the gene of interest in a number of different individuals. This can be readily carried out by using hybridization probes to identify the same genetic locus in a variety of individuals. Any and all such nucleotide variations and resulting amino acid polymorphisms or variations that are the result of natural allelic variation and that do not alter the functional activity are intended to be within the scope of the invention.

Accordingly, in another embodiment, an isolated nucleic acid molecule of the invention is at least 300 (325, 350, 375, 400, 425, 450, 500, 550, 600, 650, 700, 800, 900, 1000, or 1290) nucleotides in length and hybridizes under stringent conditions to the nucleic acid molecule comprising the nucleotide sequence, preferably the coding sequence of SEQ ID NO:1 or 2 and encodes an allelic variant or mutant of murine GPR10.

As used herein, the term "hybridizes under stringent conditions" is intended to describe conditions for hybridization and washing under which nucleotide sequences at least 60% (65%, 70%, preferably 75%) identical to each other typically remain hybridized to each other. Such stringent conditions are known to those skilled in the art and can be found in Current Protocols in Molecular Biology, John Wiley & Sons, N.Y. (1989), 6.3.1–6.3.6. A preferred, non-limiting example of stringent hybridization conditions are hybridization in 6×sodium chloride/sodium citrate (SSC) at about 45° C., followed by one or more washes in 0.2×SSC, 0.1% SDS at 50–65° C. Preferably, an isolated nucleic acid molecule of the invention that hybridizes under stringent conditions to the sequence of any of SEQ ID NO:1 or 2, corresponds to a naturally-occurring nucleic acid molecule. As used herein, a "naturally-occurring" nucleic acid molecule refers to an RNA or DNA molecule having a nucleotide sequence that occurs in nature (e.g., encodes a natural protein).

In addition to naturally-occurring allelic variants of GPR10, the skilled artisan will further appreciate that changes can be introduced by mutation thereby leading to changes in the amino acid sequence of the encoded protein, without altering the biological activity of the protein. For example, one can make nucleotide substitutions leading to amino acid substitutions at "non-essential" amino acid residues. A "non-essential" amino acid residue is a residue that can be altered from the wild-type sequence without altering the biological activity, whereas an "essential" amino acid residue is required for biological activity. For example, amino acid residues that are not conserved or only semi-conserved among homologues of various species may be non-essential for activity and thus would be likely targets for alteration. Alternatively, amino acid residues that are conserved among the homologues of various species (e.g., murine and human) may be essential for activity and thus would not be likely targets for alteration.

Accordingly, another aspect of the invention pertains to nucleic acid molecules encoding murine GPR10 that contain changes in amino acid residues that are not essential for activity. Such polypeptides differ in amino acid sequence from SEQ ID NO:3 yet retain biological activity. In one embodiment, the isolated nucleic acid molecule includes a nucleotide sequence encoding a protein that includes an amino acid sequence that is at least about 85%, 95%, 96%, 97%, 98%, or 99% identical to the amino acid sequence of SEQ ID NO:3.

An isolated nucleic acid molecule encoding a variant protein can be created by introducing one or more nucleotide substitutions, additions or deletions into the nucleotide sequence of SEQ ID NOS:1 or 2 such that one or more amino acid substitutions, additions or deletions are introduced into the encoded protein. Mutations can be introduced by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Alternatively, mutations can be introduced randomly along all or part of the coding sequence, such as by saturation mutagenesis, and the resultant mutants can be screened for biological activity to identify mutants that retain activity. Following mutagenesis, the encoded protein can be expressed recombinantly and the activity of the protein can be determined.

In one embodiment, a mutant polypeptide that is a variant of murine GPR10 can be assayed for: (1) the ability to form protein:protein interactions with proteins in a signaling pathway of murine GPR10; (2) the ability to bind a ligand of GPR10 (e.g., PrRP); or (3) the ability to bind to an intracellular target protein of GPR10. In another embodiment, the mutant polypeptide can be assayed for the ability to mediate changes in feeding behavior, body weight, or metabolism.

The present invention encompasses antisense nucleic acid molecules, i.e., molecules which are complementary to a sense nucleic acid encoding murine GPR10, e.g., complementary to the coding strand of a double-stranded cDNA molecule or complementary to an mRNA sequence. Accordingly, an antisense nucleic acid can hydrogen bond to a sense nucleic acid. The antisense nucleic acid can be complementary to an entire coding strand, or to only a portion thereof, e.g., all or part of the protein coding region (or open reading frame). An antisense nucleic acid molecule can be antisense to ail or part of a noncoding region of the coding strand of a nucleotide sequence encoding murine GPR10. The noncoding regions ("5' and 3' untranslated regions") are the 5' and 3' sequences which flank the coding region and are not translated into amino acids.

An antisense oligonucleotide can be, for example, about 5, 10, 15, 20, 25, 30, 35, 40, 45 or 50 nucleotides in length. An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a subject or generated in situ such that they hybridize with or bind to cellular mRNA and/or genomic DNA encoding GPR10 to thereby inhibit expression, e.g., by inhibiting transcription and/or translation. The hybridization can be by conventional nucleotide complementarity to form a stable duplex, or, for example, in the case of an antisense nucleic acid molecule which binds to DNA duplexes, through specific interactions in the major groove of the double helix. An example of a route of administration of antisense nucleic acid molecules of the invention includes direct injection at a tissue site. Alternatively, antisense nucleic acid molecules can be modified to target selected cells and then administered systemically. For example, for systemic administration, antisense molecules can be modified such that they specifically bind to receptors or antigens expressed on a selected cell surface, e.g., by linking the antisense nucleic acid molecules to peptides or antibodies which bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

An antisense nucleic acid molecule of the invention can be an α-anomeric nucleic acid molecule. An α-anomeric nucleic acid molecule forms specific double-stranded hybrids with complementary RNA in which, contrary to the usual β-units, the strands run parallel to each other (Gaultier et al. (1987) *Nucleic Acids Res.* 15:6625–6641). The antisense nucleic acid molecule can also comprise a 2'-o-methylribonucleotide (Inoue et al. (1987) *Nucleic Acids Res.* 15:6131–6148) or a chimeric RNA-DNA analogue (Inoue et al. (1987) *FEBS Lett.* 215:327–330).

The invention also encompasses ribozymes. Ribozymes are catalytic RNA molecules with ribonuclease activity which are capable of cleaving a single-stranded nucleic acid, such as an mRNA, to which they have a complementary region. Thus, ribozymes (e.g., hammerhead ribozymes (described in Haselhoff and Gerlach (1988) *Nature* 334:585–591)) can be used to catalytically cleave mRNA transcripts to thereby inhibit translation of the protein encoded by the mRNA. A ribozyme having specificity for a nucleic acid molecule encoding murine GPR10 can be designed based upon the nucleotide sequence of a cDNA disclosed herein. For example, a derivative of a Tetrahymena L-19 IVS RNA can be constructed in which the nucleotide sequence of the active site is complementary to the nucleotide sequence to be cleaved in a Cech et al. U.S. Pat. No. 4,987,071; and Cech et al. U.S. Pat. No. 5,116,742. Alternatively, an mRNA encoding murine GPR10 can be used to select a catalytic RNA having a specific ribonuclease activity from a pool of RNA molecules. See, e.g., Bartel and Szostak (1993) *Science* 261:1411–1418.

The invention also encompasses nucleic acid molecules which form triple helical structures. For example, expression of murine GPR10 can be inhibited by targeting nucleotide sequences complementary to the regulatory region of the gene encoding the polypeptide (e.g., the promoter and/or enhancer) to form triple helical structures that prevent transcription of the gene in target cells. See generally Helene (1991) *Anticancer Drug Des.* 6(6):569–84; Helene (1992) *Ann. N.Y. Acad. Sci.* 660:27–36; and Maher (1992) *Bioassays* 14(12):807–15.

In certain embodiments, the nucleic acid molecules of the invention can be modified at the base moiety, sugar moiety or phosphate backbone to improve, e.g., the stability, hybridization, or solubility of the molecule. For example, the deoxyribose phosphate backbone of the nucleic acids can be modified to generate peptide nucleic acids (see Hyrup et al. (1996) *Bioorganic & Medicinal Chemistry* 4(1): 5–23). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup et al. (1996), supra; Perry-O'Keefe et al. (1996) *Proc. Natl. Acad. Sci. USA* 93: 14670–675.

PNAs can be used in therapeutic and diagnostic applications. For example, PNAs can be used as antisense or antigene agents for sequence-specific modulation of gene expression by, e.g., inducing transcription or translation arrest or inhibiting replication. PNAs can also be used, e.g., in the analysis of single base pair mutations in a gene by, e.g., PNA directed PCR clamping; as artificial restriction enzymes when used in combination with other enzymes, e.g., S1 nucleases (Hyrup (1996), supra; or as probes or primers for DNA sequence and hybridization (Hyrup (1996), supra; Perry-O'Keefe et al. (1996) *Proc. Natl. Acad. Sci. USA* 93: 14670–675).

In another embodiment, PNAs can be modified, e.g., to enhance their stability or cellular uptake, by attaching lipophilic or other helper groups to PNA, by the formation of PNA-DNA chimeras, or by the use of liposomes or other techniques of drug delivery known in the art. For example, PNA-DNA chimeras can be generated which may combine the advantageous properties of PNA and DNA. Such chimeras allow DNA recognition enzymes, e.g., RNAse H and DNA polymerases, to interact with the DNA portion while the PNA portion would provide high binding affinity and specificity. PNA-DNA chimeras can be linked using linkers of appropriate lengths selected in terms of base stacking, number of bonds between the nucleobases, and orientation (Hyrup (1996), supra). The synthesis of PNA-DNA chimeras can be performed as described in Hyrup (1996), supra, and Finn et al. (1996) *Nucleic Acids Res.* 24(17):3357–63. For example, a DNA chain can be synthesized on a solid support using standard phosphoramidite coupling chemistry and modified nucleoside analogs. Compounds such as 5'-(4-methoxytrityl)amino-5'-deoxy-thymidine phosphoramidite can be used as a link between the PNA and the 5' end of DNA (Mag et al. (1989) *Nucleic Acids Res.* 17:5973–88). PNA monomers are then coupled in a stepwise manner to produce a chimeric molecule with a 5' PNA segment and a 3' DNA segment (Finn et al. (1996) *Nucleic Acids Res.* 24(17):3357–63). Alternatively, chimeric molecules can be synthesized with a 5' DNA segment and a 3' PNA segment (Peterser et al. (1975) *Bioorganic Med. Chem. Lett.* 5:1119–11124).

In other embodiments, the oligonucleotide may include other appended groups such as peptides (e.g., for targeting host cell receptors in viva), or agents facilitating transport across the cell membrane (see, e.g., Letsinger et al. (1989) *Proc. Natl. Acad. Sci. USA* 86:6553–6556; Lemaitre et al. (1987) *Proc. Natl. Acad. Sci. USA* 84:648–652; PCT Publication No. WO 88/09810) or the blood-brain barrier (see, e.g., PCT Publication No. WO 89/10134). In addition, oligonucleotides can be modified with hybridization-triggered cleavage agents (see, e.g., Krol et al. (1988) *Bio/Techniques* 6:958–976) or intercalating agents (see, e.g., Zon (1988) *Pharm. Res.* 5:539–549). To this end, the oligonucleotide may be conjugated to another molecule, e.g., a peptide, hybridization triggered cross-linking agent, transport agent, hybridization-triggered cleavage agent, etc.

V. Isolated Proteins and Antibodies

One aspect of the invention pertains co isolated proteins, and biologically active portions thereof, as well as polypeptide fragments suitable for use as immunogen to raise antibodies directed against murine GPR10. In one embodiment, native GPR10 can be isolated from cells or tissue sources by an appropriate purification scheme using standard protein purification techniques. In another embodiment, polypeptides of the invention are produced by recombinant DNA techniques. Alternative to recombinant expression, murine GPR10 can be synthesized chemically using standard peptide synthesis techniques. This section describes murine GPR10 polypeptides, antibodies directed against murine GPR10, and methods for making and using such polypeptides and antibodies. However, the same techniques can be employed to make and use human GPR10 polypeptides and anti-human GPR10 antibodies.

An "isolated" or "purified" protein or biologically active portion thereof is substantially free of cellular material or other contaminating proteins from the cell or tissue source from which the protein is derived, or substantially free of chemical precursors or other chemicals when chemically synthesized. The language "substantially free of cellular material" includes preparations of protein in which the protein is separated from cellular components of the cells from which it is isolated or recombinantly produced. Thus, protein that is substantially free of cellular material includes preparations of protein having less than about 30%, 20%, 10%, or 5% (by dry weight) of heterologous protein (also referred to herein as a "contaminating protein"). When the protein or biologically active portion thereof is recombinantly produced, it is also preferably substantially free of culture medium, i.e., culture medium represents less than about 20%, 10%, or 5% of the volume of the protein preparation. When the protein is produced by chemical synthesis, it is preferably substantially free of chemical precursors or other chemicals, i.e., it is separated from chemical precursors or other chemicals which are involved in the synthesis of the protein. Accordingly such preparations of the protein have less than about 30%, 20%, 10%, 5% (by dry weight) of chemical precursors or non-GPR10 chemicals.

Biologically active portions of murine GPR10 include polypeptides comprising amino acid sequences sufficiently identical to or derived from the amino acid sequence of the protein (e.g., the amino acid sequence shown in SEQ ID NO:3, which include fewer amino acids than the full length protein, and exhibit at least one activity of the corresponding full-length protein. Typically, biologically active portions comprise a domain or motif with at least one activity of the corresponding protein. A biologically active portion of a protein of the invention can be a polypeptide which is, for example, 10, 25, 50, 100 or more amino acids in length. Moreover, other biologically active portions, in which other regions of the protein are deleted, can be prepared by recombinant techniques and evaluated for one or more of the functional activities of the native form of murine GPR10.

Among the useful polypeptides are those having the amino acid sequence of SEQ ID NO:3. Other useful proteins are substantially identical (e.g., at least about 96%, 97%, 98%, 99%, or 99.5%) to any SEQ ID NO:3 and retain the functional activity of the protein of the corresponding naturally-occurring protein yet differ in amino acid sequence due to natural allelic variation or mutagenesis.

To determine the percent identity of two amino acid sequences or of two nucleic acid sequences, the sequences are aligned for optimal comparison purposes (e.g., gaps can be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=# of identical positions/total # of positions (e.g., overlapping positions)×100). Preferably, the two sequences are the same length.

The determination of percent homology between two sequences can be accomplished using a mathematical algorithm. A non-limiting example of a mathematical algorithm utilized for the comparison of two sequences is the algorithm of Karlin and Altschul (1990) *Proc. Natl. Acad. Sci. USA* 87:2264–2268, modified as in Karlin and Altschul (1993) *Proc. Natl. Acad. Sci. USA* 90:5873–5877. Such an algorithm is incorporated into the NBLAST and XBLAST programs of Altschul, et al. (1990) *J. Mol. Biol.* 215:403–410. BLAST nucleotide searches can be performed with the NBLAST program, score=100, wordlength=12 to obtain nucleotide sequences homologous to the murine GPR10 nucleic acid molecules of the invention. BLAST protein searches can be performed with the XBLAST program, score=50, wordlength=3 to obtain amino acid sequences homologous to murine GPR10 protein molecules of the invention. To obtain gapped alignments for comparison purposes, Gapped BLAST can be utilized as described in Altschul et al. (1997) *Nucleic Acids Res.* 25:3389–3402. Alternatively, PSI-Blast can be used to perform an iterated search which detects distant relationships between molecules. Id. When utilizing BLAST, Gapped BLAST, and PSI-Blast programs, the default parameters of the respective programs (e.g., XBLAST and NBLAST) can be used. See http://www.ncbi.nlm.nih.gov. Another non-limiting example of a mathematical algorithm utilized for the comparison of sequences is the algorithm of Myers and Miller, (1988) *CABIOS* 4:11–17. Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used.

The percent identity between two sequences can be determined using techniques similar to those described above, with or without allowing gaps. In calculating percent identity, only exact matches are counted.

The invention also provides chimeric or fusion proteins. As used herein, a "chimeric protein" or "fusion protein" comprises all or part (e.g., a biologically active fragment) of murine GPR10 operably linked to a heterologous polypeptide (i.e., a polypeptide other than the same polypeptide of the invention). Within the fusion protein, the term "operably linked" is intended to indicate that the polypeptide of the invention and the heterologous polypeptide are fused in-frame to each other. The heterologous polypeptide can be fused to the N-terminus or C-terminus of the GPR10 polypeptide.

One useful fusion protein is a GST fusion protein in which all or a portion of GPR10 is fused to the C-terminus of GST sequences. Such fusion proteins can facilitate the purification of a recombinant polypeptide. Other useful fusion proteins include fusions to FLAG™, a portion lacz, GST, calmodulin-binding peptide, His$^6$, or HA. Vectors for preparing such fusions proteins are available from Clontech, Inc. (Palo Alto, Calif.) and Stratagene, Inc. (La Jolla, Calif.).

In another embodiment, the fusion protein contains a heterologous signal sequence at its N-terminus. For example, the native signal sequence of murine GPR10 can be removed and replaced with a signal sequence from another protein. For example, the gp67 secretory sequence of the baculovirus envelope protein can be used as a heterologous signal sequence (*Current Protocols in Molecular Biology*, Ausubel et al., eds., John Wiley & Sons, 1992). Other examples of eukaryotic heterologous signal sequences include the secretory sequences of melittin and human placental alkaline phosphatase (Stratagene; La Jolla, Calif.). In yet another example, useful prokaryotic heterologous signal sequences include the phoA secretory signal (Sambrook et al., supra) and the protein A secretory signal (Pharmacia Biotech; Piscataway, N.J.).

In yet another embodiment, the fusion protein is an immunoglobulin fusion protein in which all or part of GPR10 is fused to sequences derived from a member of the immunoglobulin protein family. The immunoglobulin fusion proteins of the invention can be incorporated into pharmaceutical compositions and administered to a subject to inhibit an interaction between a ligand (soluble or membrane-bound) and a protein on the surface of a cell (receptor), to thereby suppress signal transduction in vivo. The immunoglobulin fusion protein can be used to affect the bioavailability of a cognate ligand of GPR10. Inhibition of ligand/receptor interaction may be useful therapeutically for modulating feeding behavior, body weight, and/or metabolic rate. Moreover, the immunoglobulin fusion proteins of the invention can be used as immunogen to produce antibodies directed against GPR10 in a subject, to purify ligands and in screening assays to identify molecules which inhibit the interaction of receptors with ligands.

Chimeric and fusion protein of the invention can be produced by standard recombinant DNA techniques. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (see, e.g., Ausubel et al., supra). Moreover, many expression vectors are commercially available that already encode a fusion moiety (e.g., a GST polypeptide). A nucleic acid encoding GPR10 can be cloned into such an expression vector such that the fusion moiety is linked in-frame to the polypeptide of the invention.

The present invention also pertains to variants of GPR10. Such variants have an altered amino acid sequence which can function as either agonists (mimetics) or as antagonists. Variants can be generated by mutagenesis, e.g., discrete point mutation or truncation. An agonist can retain substantially the same, or a subset, of the biological activities of the naturally occurring form of the protein. An antagonist of a protein can inhibit one or more of the activities of the naturally occurring form of the protein by, for example, competitively binding to a downstream or upstream member of a cellular signaling cascade which includes the protein of interest. Thus, specific biological effects can be elicited by treatment with a variant of limited function. Treatment of a subject with a variant having a subset of the biological activities of the naturally occurring form of the protein can have fewer side effects in a subject relative to treatment with the naturally occurring form of the protein.

Variants of a protein of the invention which function as either agonists (mimetics) or as antagonists can be identified by screening combinatorial libraries of mutants, e.g., truncation mutants, of the protein of the invention for agonist or antagonist activity. In one embodiment, a variegated library of variants is generated by combinatorial mutagenesis at the nucleic acid level and is encoded by a variegated gene library. A variegated library of variants can be produced by, for example, enzymatically ligating a mixture of synthetic oligonucleotides into gene sequences such that a degenerate set of potential protein sequences is expressible as individual polypeptides, or alternatively, as a set of larger fusion proteins (e.g., for phage display). There are a variety of methods which can be used to produce libraries of potential variants of the polyepeptides of the invention from a degenerate oligonucleotide sequence. Methods for synthesizing degenerate oligonucleotides are known in the art (see, e.g., Narang (1983) *Tetrahedron* 39:3; Itakura et al. (1984) *Annu. Rev. Biochem.* 53:323; Itakura et al. (1984) *Science* 198:1056; Ike et al. (1983) *Nucleic Acid Res.* 11:477).

In addition, libraries of fragments of the coding sequence of GPR10 can be used to generate a variegated population of polypeptides for screening and subsequent selection of variants. For example, a library of coding sequence fragments can be generated by treating a double stranded PCR fragment of the coding sequence of interest with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with Si nuclease, and ligating the resulting fragment library into an expression vector. By this method, an expression library can be derived which encodes N-terminal and internal fragments of various sizes of the protein of interest.

Several techniques are known in the art for screening gene products of combinatorial libraries made by point mutations or truncation, and for screening cDNA libraries for gene products having a selected property. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected.

Recursive ensemble mutagenesis (REM), a technique which enhances the frequency of functional mutants in the libraries, can be used in combination with the screening assays to identify variants of a protein of the invention (Arkin and Yourvan (1992) *Proc. Natl. Acad. Sci. USA* 89:7811–7815; Delgrave et al. (1993) *Protein Engineering* 6(3):327–331).

An isolated GPR10 polypeptide can be used as an immunogen to generate antibodies using standard techniques for polyclonal and monoclonal antibody preparation. The full-length polypeptide or protein can be used or, alternatively, the invention provides antigenic peptide fragments for use as immunogen. The antigenic peptide of a protein of the invention comprises at least 8 (preferably 10, 15, 20, or 30) amino acid residues of the amino acid sequence of SEQ ID NO:3 and encompasses an epitope of the protein such that an antibody raised against the peptide forms a specific immune complex with the protein. Useful eptiopes encompassed by the antigenic peptide are often, but not exclusively, regions that are located on the surface of the protein, e.g., hydrophilic regions.

An immunogen typically is used to prepare antibodies by immunizing a suitable subject, (e.g., rabbit, goat, mouse or other mammal). An appropriate immunogenic preparation can contain, for example, recombinantly expressed chemically synthesized polypeptide. The preparation can further include an adjuvant, such as Freund's complete or incomplete adjuvant, or similar immunostimulatory agent.

Accordingly, another aspect of the invention pertains to antibodies directed against GPR10. The term "antibody" as used herein refers to immunoglobulin molecules and immunologically active portions of immunoglobulin molecules, i.e., molecules that contain an antigen binding site which specifically binds an antigen, such as murine GPR10. A molecule which specifically binds to a given polypeptide of the invention is a molecule which binds the polypeptide, but does not substantially bind other molecules in a sample, e.g., a biological sample, which naturally contains the polypeptide. Examples of immunologically active portions of immunoglobulin molecules include F(ab) and F(ab')$_2$ fragments which can be generated by treating the antibody with an enzyme such as pepsin. The invention provides polyclonal and monoclonal antibodies. The term "monoclonal antibody" or "monoclonal antibody composition", as used herein, refers to a population of antibody molecules that contain only one species of an antigen binding site capable of immunoreacting with a particular epitope.

Polyclonal antibodies can be prepared as described above by immunizing a suitable subject with murine GPR10 as an immunogen. The antibody titer in the immunized subject can be monitored over time by standard techniques, such as with an enzyme linked immunosorbent assay (ELISA) using immobilized polypeptide. If desired, the antibody molecules can be isolated from the mammal (e.g., from the blood) and further purified by well-known techniques, such as protein A chromatography to obtain the IgG fraction. At an appropriate time after immunization, e.g., when the specific antibody titers are highest, antibody-producing cells can be obtained from the subject and used to prepare monoclonal antibodies by standard techniques, such as the hybridoma technique originally described by Kohler and Milstein (1975) *Nature* 256:495–497, the human B cell hybridoma technique (Kozbor et al. (1983) *Immunol. Today* 4:72), the EBVhybridoma technique (Cole et al. (1985), *Monoclonal Antibodies and Cancer Therapy*, Alan R. Liss, Inc., pp. 77–96) or trioma techniques. The technology for producing hybridomas is well known (see generally *Current Protocols in Immunology* (1994) Coligan et al. (eds.) John Wiley & Sons, Inc., New York, N.Y.). Hybridoma cells producing a monoclonal antibody of the invention are detected by screening the hybridoma culture supernatants for antibodies that bind the polypeptide of interest, e.g., using a standard ELISA assay.

Alternative to preparing monoclonal antibody-secreting hybridomas, a monoclonal antibody directed against murine GPR10 can be identified and isolated by screening a recombinant combinatorial immunoglobulin library (e.g., an antibody phage display library) with the polypeptide of interest. Kits for generating and screening phage display libraries are commercially available (e.g., the Pharmacia *Recombinant Phage Antibody System*, Catalog No. 27–9400–01; and the Stratagene SurfZAP™ Phage Display Kit, Catalog No. 240612). Additionally, examples of methods and reagents particularly amenable for use in generating and screening antibody display library can be found in, for example, U.S. Pat. No. 5,223,409; PCT Publication No. WO 92/18619; PCT Publication No. WO 91/17271; PCT Publication No. WO 92/20791; PCT Publication No. WO 92/15679; PCT Publication No. WO 93/01288; PCT Publication No. WO 92/01047; PCT Publication No. WO 92/09690; PCT Publication No. WO 90/02809; Fuchs et al. (1991) *Bio/Technology* 9:1370–1372; Hay et al. (1992) *Hum. Antibod. Hybridomas* 3:81–85; Huse et al. (1989) *Science* 246:1275–1281; Griffiths et al. (1993) *EMBO J.* 12:725–734.

Additionally, recombinant antibodies, such as chimeric and humanized monoclonal antibodies, comprising both human and non-human portions, which can be made using standard recombinant DNA techniques, are within the scope of the invention. Such chimeric and humanized monoclonal antibodies can be produced by recombinant DNA techniques known in the art, for example using methods described in PCT Publication No. WO 87/02671; European Patent Application 184,187; European Patent Application 171,496; European Patent Application 173,494; PCT Publication No. WO 86/01533; U.S. Pat. No. 4,816,567; European Patent Application 125,023; Better et al. (1988) *Science* 240:1041–1043; Liu et al. (1987) *Proc. Natl. Acad. Sci. USA* 84:3439–3443; Liu et al. (1987) *J. Immunol.* 139:3521–3526; Sun et al. (1987) *Proc. Natl. Acad. Sci. USA* 84:214–218; Nishimura et al. (1987) *Canc. Res.* 47:999–1005; Wood et al. (1985) *Nature* 314:446–449; and Shaw et al. (1988) *J. Natl. Cancer Inst.* 80:1553–1559); Morrison (1985) *Science* 229:1202–1207; Oi et al. (1986) *Bio/Techniques* 4:214; U.S. Pat. No. 5,225,539; Jones et al. (1986) *Nature* 321:552–525; Verhoeyan et al. (1988) *Science* 239:1534; and Beidler et al. (1988) *J. Immunol.* 141:4053–4060.

Completely human antibodies are particularly desirable for therapeutic treatment of human patients. Such antibodies can be produced using transgenic mice which are incapable of expressing endogenous immunoglobulin heavy and light chains genes, but which can express human heavy and light chain genes. The transgenic mice are immunized in the normal fashion with a selected antigen, e.g., all or a portion of murine GPR10. Monoclonal antibodies directed against the antigen can be obtained using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA and IgE antibodies. For an overview of this technology for producing human antibodies, see Lonberg and Huszar (1995, *Int. Rev. Immunol.* 13:65–93). For a detailed discussion of this technology for producing human antibodies and human monoclonal antibodies and protocols for producing such antibodies, see, e.g., U.S. Pat. No. 5,625,126; U.S. Pat. No. 5,633,425; U.S. Pat. No. 5,569,825; U.S. Pat. No. 5,661,016; and U.S. Pat. No. 5,545,806. In addition, companies such as Abgenix, Inc. (Freemont, Calif.), can be engaged to provide human antibodies directed against a selected antigen using technology similar to that described above. Completely human antibodies which recognize a selected epitope can be generated using a technique referred to as "guided selection." In this approach a selected non-human monoclonal antibody, e.g., a murine antibody, is used to guide the selection of a completely human antibody recognizing the same epitope.

An antibody directed against murine GPR10 (e.g., monoclonal antibody) can be used to isolate the polypeptide by standard techniques, such as affinity chromatography or immunoprecipitation. Moreover, such an antibody can be used to detect the protein (e.g., in a cellular lysate or cell supernatant) in order to evaluate the abundance and pattern of expression of the polypeptide. The antibodies can also be used diagnostically to monitor protein levels in tissue as part of a clinical testing procedure, e.g., to, for example, determine the efficacy of a given treatment regimen. Detection can be facilitated by coupling the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$ or $^{3}H$.

VI. Recombinant Expression Vectors and Host Cells

Another aspect of the invention pertains to vectors (e.g., expression vectors) containing a nucleic acid encoding murine GPR10 (or a portion thereof). As used herein, the term "vector" refers to a nucleic acid molecule capable of transporting another nucleic acid to which it has been linked. One type of vector is a "plasmid," which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors, expression vectors, are capable of directing the expression of genes to which they are operably linked. In general, expression vectors of utility in recombinant DNA techniques are often in the form of plasmids (vectors). However, the invention is intended to include such other forms of expression vectors, such as viral vectors (e.g., replication defective retroviruses, adenoviruses and adeno-associated viruses), which serve equivalent functions. This section describes vectors and host cells harboring murine GPR10 nucleic acids and variants thereof and methods for their production and use. However, the same techniques can be employed to make and use vectors and host cells harboring human GPR10 nucleic acids.

The recombinant expression vectors of the invention comprise a nucleic acid of the invention in a form suitable for expression of the nucleic acid in a host cell. This means that the recombinant expression vectors include one or more regulatory sequences, selected on the basis of the host cells to be used for expression, which is operably linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel, *Gene Expression Technology: Methods in Enzymology* 185, Academic Press, San Diego, Calif. (1990). Regulatory sequences include those which direct constitutive expression of a nucleotide sequence in many types of host cell and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, etc. The expression vectors of the invention can be introduced into host cells to thereby produce proteins or peptides, including fusion proteins or peptides, encoded by nucleic acids as described herein.

The recombinant expression vectors of the invention can be designed for expression of murine GPR10 in prokaryotic or eukaryotic cells, e.g., bacterial cells such as *E. coli*, insect cells (using baculovirus expression vectors), yeast cells or mammalian cells. Suitable host cells are discussed further in Goeddel, supra. Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith and Johnson (1988) *Gene* 67:31–40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein.

Examples of suitable inducible non-fusion *E. coli* expression vectors include pTrc (Amann et al., (1988) *Gene* 69:301–315) and pET 11d (Studier et al., *Gene Expression Technology: Methods in Enzymology* 185, Academic Press, San Diego, Calif. (1990) 60–89). Target gene expression from the pTrc vector relies on host RNA polymerase transcription from a hybrid trp-lac fusion promoter. Target gene expression from the pET 11d vector relies on transcription from a T7 gn10-lac fusion promoter mediated by a coexpressed viral RNA polymerase (T7 gn1). This viral polymerase is supplied by host strains BL21(DE3) or HMS174 (DE3) from a resident γ prophage harboring a T7 gn1 gene under the transcriptional control of the lacUV 5 promoter.

One strategy to maximize recombinant protein expression in *E. coli* is to express the protein in a host bacteria with an impaired capacity to proteolytically cleave the recombinant protein (Gottesman, *Gene Expression Technology: Methods in Enzymology* 185, Academic Press, San Diego, Calif. (1990) 119–128). Another strategy is to alter the nucleic acid sequence of the nucleic acid to be inserted into an expression vector so that the individual codons for each amino acid are those preferentially utilized in *E. coli* (Wada et al. (1992) *Nucleic Acids Res.* 20:2111–2118). Such alteration of nucleic acid sequences of the invention can be carried out by standard DNA synthesis techniques.

In another embodiment, the expression vector is a yeast expression vector. Examples of vectors for expression in yeast *S. cerivisae* include pYepSec1 (Baldari et al. (1987) *EMBO J*. 6:229–234), pMFa (Kurjan and Herskowitz, (1982) *Cell* 30:933–943), pJRY88 (Schultz et al. (1987) *Gene* 54:113–123), pYES2 (Invitrogen Corporation, San Diego, Calif.), and pPicZ (InVitrogen Corp, San Diego, Calif.).

Alternatively, the expression vector is a baculovirus expression vector. Baculovirus vectors available for expression of proteins in cultured insect cells (e.g., Sf 9 cells) include the pAc series (Smith et al. (1983) *Mol. Cell Biol*. 3:2156–2165) and the pVL series (Lucklow and Summers (1989) *Virology* 170:31–39).

In yet another embodiment, a nucleic acid of the invention is expressed in mammalian cells using a mammalian expression vector. Examples of mammalian expression vectors include pCDM8 (Seed (1987) *Nature* 329:840) and pMT2PC (Kaufman et al. (1987) *EMBO J*. 6:187–195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells see chapters 16 and 17 of Sambrook et al., supra.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al. (1987) *Genes Dev*. 1:268–277), lymphoid-specific promoters (Calame and Eaton (1988) *Adv. Immunol*. 43:235–275), in particular promoters of T cell receptors (Winoto and Baltimore (1989) *EMBO J*. 8:729–733) and immunoglobulins (Banerji et al. (1983) *Cell* 33:729–740; Queen and Baltimore (1983) *Cell* 33:741–748), neuronspecific promoters (e.g., the neurofilament promoter; Byrne and Ruddle (1989) *Proc. Natl. Acad. Sci. USA* 86:5473–5477), pancreas-specific promoters (Edlund et al. (1985) *Science* 230:912–916), and mammary gland-specific promoters (e.g., milk whey promoter; U.S. Pat. No. 4,873, 316 and European Application Publication No. 264,166). Developmentally-regulated promoters are also encompassed, for example the murine hox promoters (Kessel and Gruss (1990) *Science* 249:374–379) and the α-fetoprotein promoter (Campes and Tilghman (1989) *Genes Dev.* 3:537–546).

The invention further provides a recombinant expression vector comprising a DNA molecule of the invention cloned into the expression vector in an antisense orientation. That is, the DNA molecule is operably linked to a regulatory sequence in a manner which allows for expression (by transcription of the DNA molecule) of an RNA molecule which is antisense to the mRNA encoding murine GPR10. Regulatory sequences operably linked to a nucleic acid cloned in the antisense orientation can be chosen which direct the continuous expression of the antisense RNA molecule in a variety of cell types, for instance viral promoters and/or enhancers, or regulatory sequences can be chosen which direct constitutive, tissue specific or cell type specific expression of antisense RNA. The antisense expression vector can be in the form of a recombinant plasmid, phagemid or attenuated virus in which antisense nucleic acids are produced under the control of a high efficiency regulatory region, the activity of which can be determined by the cell type into which the vector is introduced. For a discussion of the regulation of gene expression using antisense genes see Weintraub et al. (*Reviews—Trends in Genetics*, Vol. 1(1) 1986).

Another aspect of the invention pertains to host cells into which a recombinant expression vector of the invention has been introduced. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell (e.g., *E. coli*, insect cells, yeast or mammalian cells).

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid into a host cell, including calcium phosphate or calcium chloride co-precipitation, DEAE-dextran-mediated transfection, lipofection, or electroporation. Suitable methods for transforming or transfecting host cells can be found in Sambrook, et al. (supra), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., for resistance to antibiotics) is generally introduced into the host cells along with the gene of interest. Useful selectable markers include those which confer resistance to drugs, such as G418, hygromycin and Imethotrexate. Cells stably transfected with the introduced nucleic acid can be identified by drug selection (e.g., cells that have incorporated the selectable marker gene will survive, while the other cells die).

A host cell of the invention, such as a prokaryotic or eukaryotic host cell in culture, can be used to produce GPR10. Accordingly, the invention further provides methods for producing GPR10 using the host cells of the invention. In one embodiment, the method comprises culturing the host cell of invention (into which a recombinant expression vector encoding GPR10 has been introduced) in a suitable medium such that the polypeptide is produced. In another embodiment, the method further comprises isolating the polypeptide from the medium or the host cell.

The host cells of the invention can also be used to produce nonhuman t-ansgenic animals. For example, in one embodiment, a host cell of the invention is a fertilized oocyte or an embryonic stem cell into which a sequences encoding GPR10 have been introduced. Such host cells can then be used to create non-human transgenic animals in which exogenous sequences encoding murine GPR10 have been introduced into their genome or homologous recombinant animals in which endogenous encoding GPR10 sequences have been altered. Such animals are useful for studying the function and/or activity of the polypeptide and for identifying and/or evaluating modulators of polypeptide activity. As used herein, a "transgenic animal" is a non-human animal, e.g., a mammal, particularly a rodent such as a rat or mouse, in which one or more of the cells of the animal includes a transgene. Other examples of transgenic animals include non-human primates, sheep, dogs, cows, goats, chickens, amphibians, etc. A transgene is exogenous DNA which is integrated into the genome of a cell from which a transgenic animal develops and which remains in the genome of the mature animal, thereby directing the expression of an encoded gene product in one or more cell types or tissues of the transgenic animal. As used herein, an "homologous recombinant animal" is a non-human animal, e.g., a mammal, particularly a mouse, in which an endogenous gene has been altered by homologous recombination between the endogenous gene and an exogenous DNA molecule introduced into a cell of the animal, e.g., an embryonic cell of the animal, prior to development of the animal.

A transgenic animal of the invention can be created by introducing nucleic acid encoding murine GPR10 (or a homologue thereof) into the male pronuclei of a fertilized oocyte, e.g., by microinjection, retroviral infection, and allowing the oocyte to develop in a pseudopregnant female foster animal. Intronic sequences and polyadenylation signals can also be included in the transgene to increase the efficiency of expression of the transgene. A tissue-specific regulatory sequence(s) can be operably linked to the transgene to direct expression of the polypeptide of the invention to particular cells. Methods for generating transgenic animals via embryo manipulation and microinjection, particularly animals such as mice, have become conventional in the art and are described, for example, in U.S. Pat. Nos. 4,736, 866 and 4,870,009, U.S. Pat. No. 4,873,191 and in Hogan, *Manipulating the Mouse Embryo*, (Cold Spring Harbor Laboratory Press, Cold Spring Harbor, N.Y., 1986). Similar methods are used for production of other transgenic animals. A transgenic founder animal can be identified based upon the presence of the transgene in its genome and/or expression of mRNA encoding the transgene in tissues or cells of the animals. A transgenic founder animal can then be used to breed additional animals carrying the transgene. Moreover, transgenic animals carrying the transgene can further be bred to other transgenic animals carrying other transgenes.

To create an homologous recombinant animal, a vector is prepared which contains at least a portion of a gene encoding murine GPR10 into which a deletion, addition or substitution has been introduced to thereby alter, e.g., functionally disrupt, the gene. In one embodiment, the vector is designed such that, upon homologous recombination, the endogenous gene is functionally disrupted (i.e., no longer encodes a functional protein; also referred to as a "knock out" vector). Alternatively, the vector can be designed such that, upon homologous recombination, the endogenous gene is mutated or otherwise altered but still encodes functional protein (e.g., the upstream regulatory region can be altered to thereby alter the expression of the endogenous protein). In the homologous recombination vector, the altered portion of the gene is flanked at its 5' and 3' ends by additional nucleic acid of the gene to allow for homologous recombination to occur between the exogenous gene carried by the vector and an endogenous gene in an embryonic stem cell. The additional flanking nucleic acid sequences are of sufficient length for successful homologous recombination with the endogenous gene. Typically, several kilobases of flanking DNA (both at the 5' and 3' ends) are included in the vector (see, e.g., Thomas and Capecchi (1987) *Cell* 51:503 for a description of homologous recombination vectors). The vector is introduced into an embryonic stem cell line (e.g., by electroporation) and cells in which the introduced gene has homologously recombined with the endogenous gene are selected (see, e.g., Li et al. (1992) *Cell* 69:915). The selected cells are then injected into a blastocyst of an animal (e.g., a mouse) to form aggregation chimeras (see, e.g., Bradley in *Teratocarcinomas and Embryonic Stem Cells: A Practical Approach*, Robertson, ed. (IRL, Oxford, 1987) pp. 113–152). A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA by germline transmission of the transgene. Methods for constructing homologous recombination vectors and homologous recombinant animals are described further in Bradley (1991) *Current Opinion in Bio/Technology* 2:823–829 and in PCT Publication Nos. WO 90/11354, WO 91/01140, WO 92/0968, and WO 93/04169.

In another embodiment, transgenic non-human animals can be produced which contain selected systems which allow for regulated expression of the transgene. One example of such a system is the cre/loxP recombinase system of bacteriophage P1. For a description of the cre/loxp recombinase system, see, e.g., Lakso et al. (1992) *Proc. Natl. Acad. Sci. USA* 89:6232–6236. Another example of a recombinase system is the FLP recombinase system of Saccharomyces cerevisiae (O'Gorman et al. (1991) *Science* 251:1351–1355. If a cre/loxP recombinase system is used to regulate expression of the transgene, animals containing transgenes encoding both the Cre recombinase and a selected protein are required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut et al. (1997) *Nature* 385:810–813 and PCT Publication Nos. WO 97/07668 and WO 97/07669.

VII. Methods of Treatment

The present invention provides for both prophylactic and therapeutic methods for modulating body weight, e.g., by altering feeding behavior or metabolic rate.

In one aspect, the invention provides a method for modulating body weight by administering an agent which modulates an activity of GPR10. Such methods are useful for modulating body weight both in patients having aberrant expression or activity of GPR10 or other patients which would benefit from administration of an agent which modulates activity of GPR10. Depending on the needs of the patient a GPR10 agonist or antagonist can be used for treating the subject.

Antagonists of GPR10 activity or compounds which reduce expression of GPR10 are useful for treatment of high body weight, e.g., obesity, because they can be used to reduce body weight. Similarly, compounds which decrease the activity or expression of a protein in the GPR10 signalling pathway are useful for treatment of high body weight. Conversely, agonists of GPR10 activity or compounds which increase the expression of GPR10 are useful for treatment of low body weight, e.g., cachexia, because they can be used to increase body weight. Compounds which increase the activity or expression of a protein in the GPR10 signalling pathway are useful for treatment of low body weight.

The modulatory method of the invention involves contacting a cell with an agent that modulates one or more of the activities of GPR10. An agent that modulates activity can be an agent as described herein, such as a nucleic acid or a protein, a naturally-occurring cognate ligand of the polypeptide, a peptide, a peptidomimetic, or other small molecule. In one embodiment, the agent stimulates one or more of the biological activities of GPR10. Examples of such stimulatory agents include the active GPR10 polypeptides and a nucleic acid molecules encoding a portion of GPR10. In another embodiment, the agent inhibits one or more of the biological activities of GPR10. Examples of such inhibitory agents include antisense nucleic acid molecules and antibodies. These modulatory methods can be performed in vitro (e.g., by culturing the cell with the agent) or, alternatively, in vivo (e.g, by administering the agent to a subject). As such, the present invention provides methods of treating an individual afflicted with a disease or disorder characterized by unwanted expression or activity of GPR10 or a protein in the GPR10 signaling pathway. In one embodiment, the method involves administering an agent (e.g., an agent identified by a screening assay described herein), or combination of agents that modulates (e.g., upregulates or downregulates) expression or activity of GPR10 or a protein in the GPR10 signalling pathway. In another embodiment, the method involves administering a modulator of GPR10 as therapy to compensate for reduced or undesirably low expression or activity of GPR10 or a protein in the GPR10 signalling pathway.

Stimulation of activity or expression is desirable in situations in which activity or expression is abnormally low downregulated and/or in which increased activity is likely to have a beneficial effect. Conversely, inhibition of activity or expression is desirable in situations in which activity or expression is abnormally high or upregulated and/or in which decreased activity is likely to have a beneficial effect.

This invention is further illustrated by the following examples which should not be construed as limiting. The contents of all references, patents and published patent applications cited throughout this application are hereby incorporated by reference.

VIII. Pharmaceutical Compositions

This invention further pertains to novel agents identified by the above-described screening assays and uses thereof for treatments as described herein.

The nucleic acid molecules, polypeptides, and antibodies (also referred to herein as "active compounds") of the invention can be incorporated into pharmaceutical compositions suitable for administration. Such compositions typically comprise the nucleic acid molecule, protein, or antibody and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

The invention includes pharmaceutical compositions comprising a modulator of GPR10 expression or activity (and/or a modulator of the activity or expression of a protein in the GPR10 signalling pathway) as a well as methods for preparing such compositions by combining one or more such modulators and a pharmaceutically acceptable carrier. Also within the invention are pharmaceutical compositions comprising a modulator identified using the screening assays of the invention packaged with instructions for use. For modulators that are antagonists of GPR10 activity or which reduce GPR10 expression, the instructions would specify use of the pharmaceutical composition for treatment of high body weight (e.g., reduction of body weight). For modulators that are agonists of GPR10 activity or increase GPR10 expression, the instructions would specify use of the pharmaceutical composition for treatment of low body weight (i.e., reduction of body weight).

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersions. For intravenous administration, suitable carriers include physiological saline, bacteriostatic water, Cremophor EL™ (BASF; Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., a polypeptide or antibody) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from a pressurized container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in he art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The nucleic acid molecules of the invention can be inserted into vectors and used as gene therapy vectors. Gene therapy vectors can be delivered to a subject by, for example, intravenous injection, local administration (U.S. Pat. No. 5,328,470) or by stereotactic injection (see, e.g., Chen et al. (1994) *Proc. Natl. Acad. Sci. USA* 91:3054–3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g. retroviral vectors, the pharmaceutical preparation can include one or more cells which produce the gene delivery system.

The pharmaceutical compositions can be included in a container, pack, or dispenser together with instructions for administration. For pharmaceutical compositions which include an antagonist of GPR10 activity, a compound which reduces expression of GPR10, or a compound which reduces expression or activity of a protein in the GPR10 signaling pathway (or some combination thereof), the instructions for administration will specify use of the composition for decreasing body weight. For pharmaceutical compositions which include an agonist of GPR10 activity, a compound which increases expression of GPR10, or a compound which increases expression or activity of a protein in the GPR10 signaling pathway (or some combination thereof), the instructions for administration will specify use of the composition for increasing body weight.

EXAMPLES

Example 1

GPR10 is Expression in Regions of the Hypothalamus that Regulate Feeding Behavior The distribution of GPR10 mRNA in mouse brain was examined as follows. Mouse brain was frozen with powdered dry ice, and cryostat sections were cut at 10 $\mu$m thickness through hypothalamus region, mounted on superfrost plus sides (VWR) and stored at $-80°$ until needed.

Prior to analysis, mouse brain sections were air dried for 20 minutes and then incubated with ice cold 4% PFA (paraformaldehyde)/1×PBS for 10 minutes. The slides were then washed with 1×PBS twice (5 minutes each time), incubated with 0.25% acetic anhydride/1 M triethanolamine for 10 minutes, washed with PBS for 5 minutes and dehydrated with 70%, 80%, 95% and 100% ethanol (1 minute each). Sections were incubated with chloroform for 5 minutes, rehydrated with 100% and 95% ethanol, then air dried. Hybridizations were performed with $^{35}$S-radiolabeled ($5 \times 10^7$ cpm/ml) cRNA probes in the presence of 50% formamide, 10% dextran sulfate, 1×Denhardt's solution, 600 mm NaCl, 10 mm DTT, 0.25% SDS and 100 $\mu$g/ml RNase A in TNE at 37° C. for 30 minutes, washed in TNE for 10 minutes, incubated once in 2×SSC at 60° for 1 hour, once in 0.2×SSC at 60° for 1 hour, 0.2×SSC at 65° for 1 hour and dehydrated with 50%, 70%, 80%, 95% and 100% ethanol. Localization of mRNA transcripts was detected by dipping slides in Kodak NBT-2 photoemulsion and exposing for 14 days at 4° C., followed by development with Kodak Dektol developer. Slides were counterstained with haemotoxylin and eosin and photographed. Controls for the in situ hybridization experiments included the use of a sense probe which showed no signal above background levels.

This analysis revealed that GPR10 mRNA is expressed within the arcuate nucleus and the ventral/medial hypothalamus, both of which are implicated in control of feeding behavior.

Example 2

PrRP, a GPR10 Ligand, Stimulates Food Intake

A 31 amino acid amidated synthetic peptide having the sequence of rat PrRP (SRAHQHSMETRTP-DINPAWYTGRGIRPVGRF-NH$_2$; SEQ ID NO:4; Hinuma et al., (1998) *Nature* 393:272–76) was used to examine the effect of GPR10 modulators on food intake.

Male and female lean and male obese ob/ob C57BL/6J mice were individually housed in macrolon cages (22±2° C.; 12:12 hr light:dark cycle with lights off at 6 pm). Tap water and mouse chow were given ad libitum. Mice were stereoaxically implanted with a chronic guide cannula aimed to the third ventricle (intracerebroventricular) one week prior to the initiation of the experiment.

Mice (15/group) were treated with 0.1, 1, 5, 10 mg of PrRP peptide or saline (control) by intracerebroventricular injections at 9:00 am. Food intake was measured for two hours after treatment.

Figure 4:
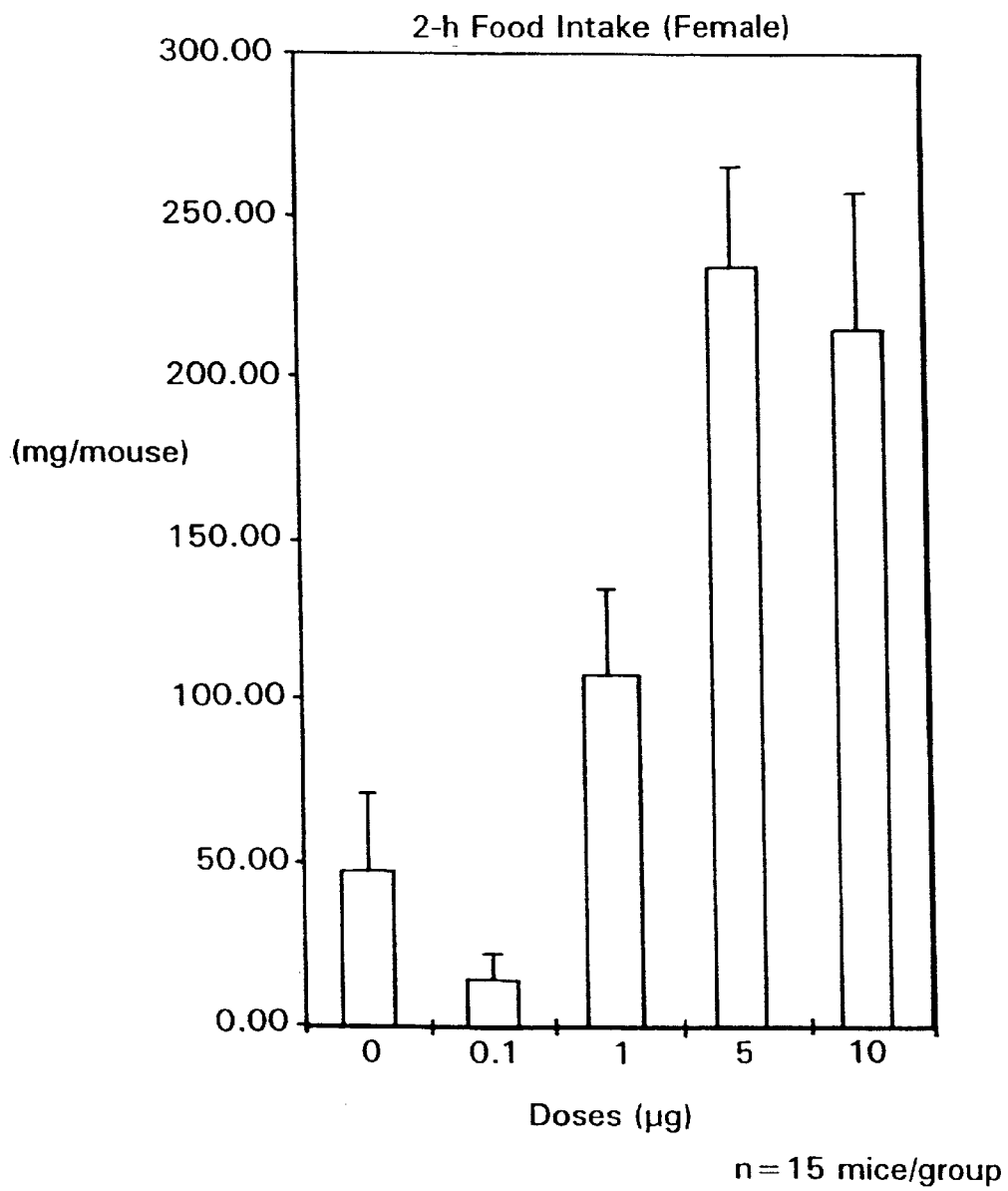
FIG. 4 is a graph illustrating the results of an experiment examining the effect of PrRP on the feeding behavior of lean female mice.
Figure 5:
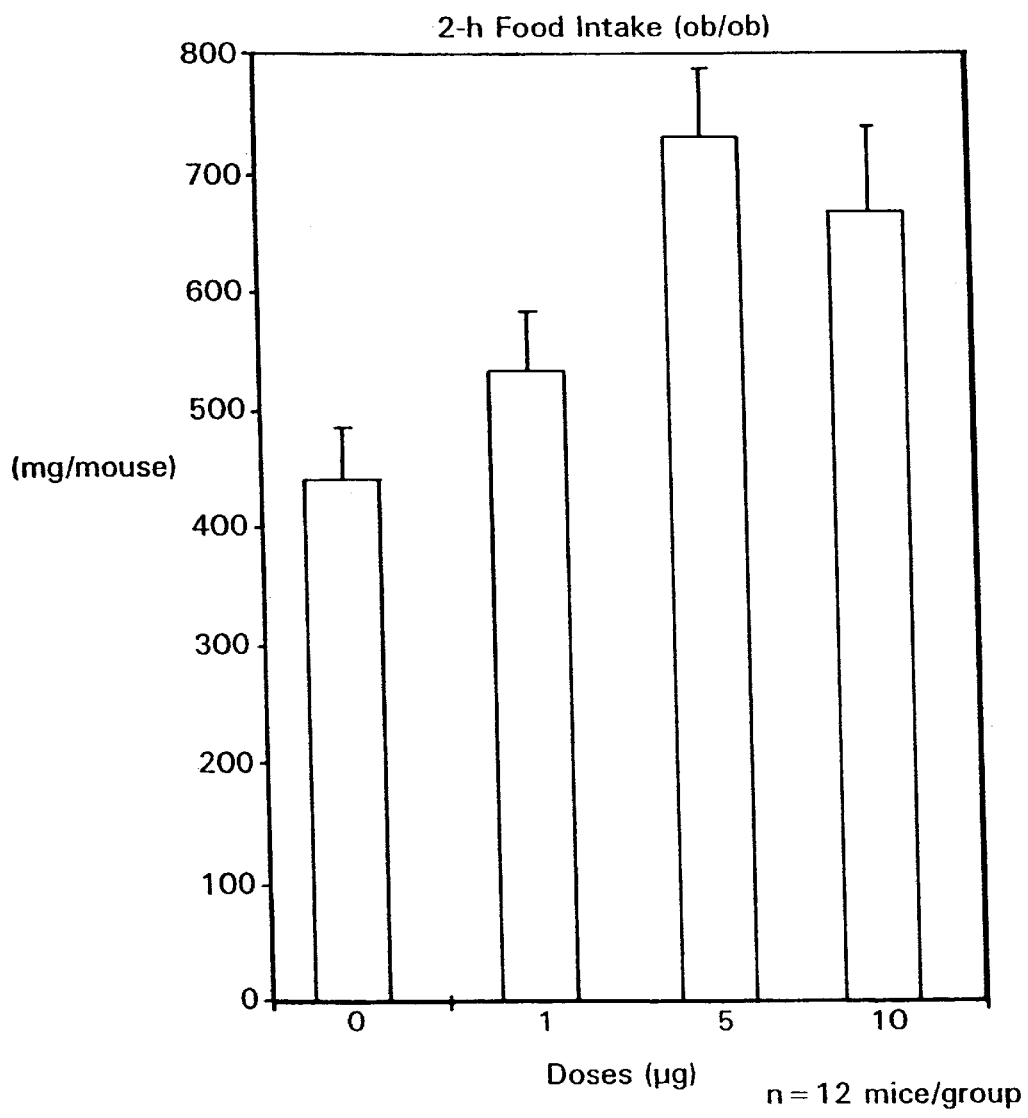
FIG. 5 is a graph illustrating the results of an experiment examining the effect of PrRP on the feeding behavior of male ob/ob mice

These experiments demonstrated that PrRP increased food intake in lean male mice (FIG. 3), lean female mice (FIG. 4) and male ob/ob (FIG. 5) mice.

Example 3

PrRP Increases Metabolic Rate

The effect of a 5 $\mu$g dose of PrRP on the metabolic rate of male mice denied or permitted access to food was investigated as follows. Male C57BL/6J mice maintained as described above were placed in an open-circuit calorimeter coupled to a feeding monitor. The mice were administered 5 $\mu$g of PrRP or saline intracerebroventricularly at 1 hr and 45 min after the start of metabolic monitoring. One group (n=6) of mice was allowed access to food and one group of mice (n=6) was not allowed access to food. Respiratory quotient was calculated as the ratio of $CO_2$ production/$O_2$ consumption. Metabolic rate (kcal/g/h) was computed based on $O_2$ consumption and respiratory rate quotient.

Figure 6:
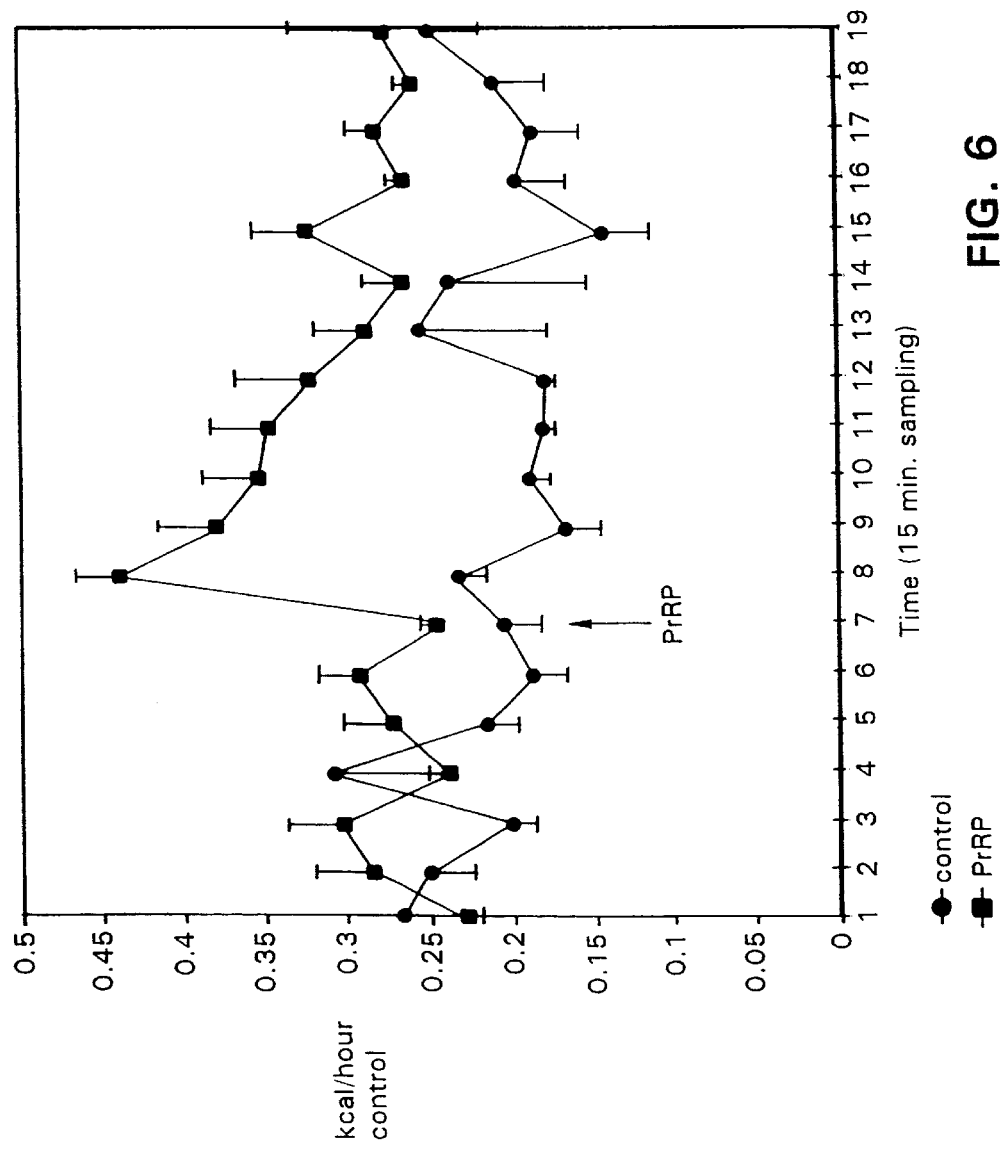
FIG. 6 is a graph illustrating the results of an experiment examining the effect of PrRP on the metabolic rate of lean male mice denied access to food.
Figure 7:
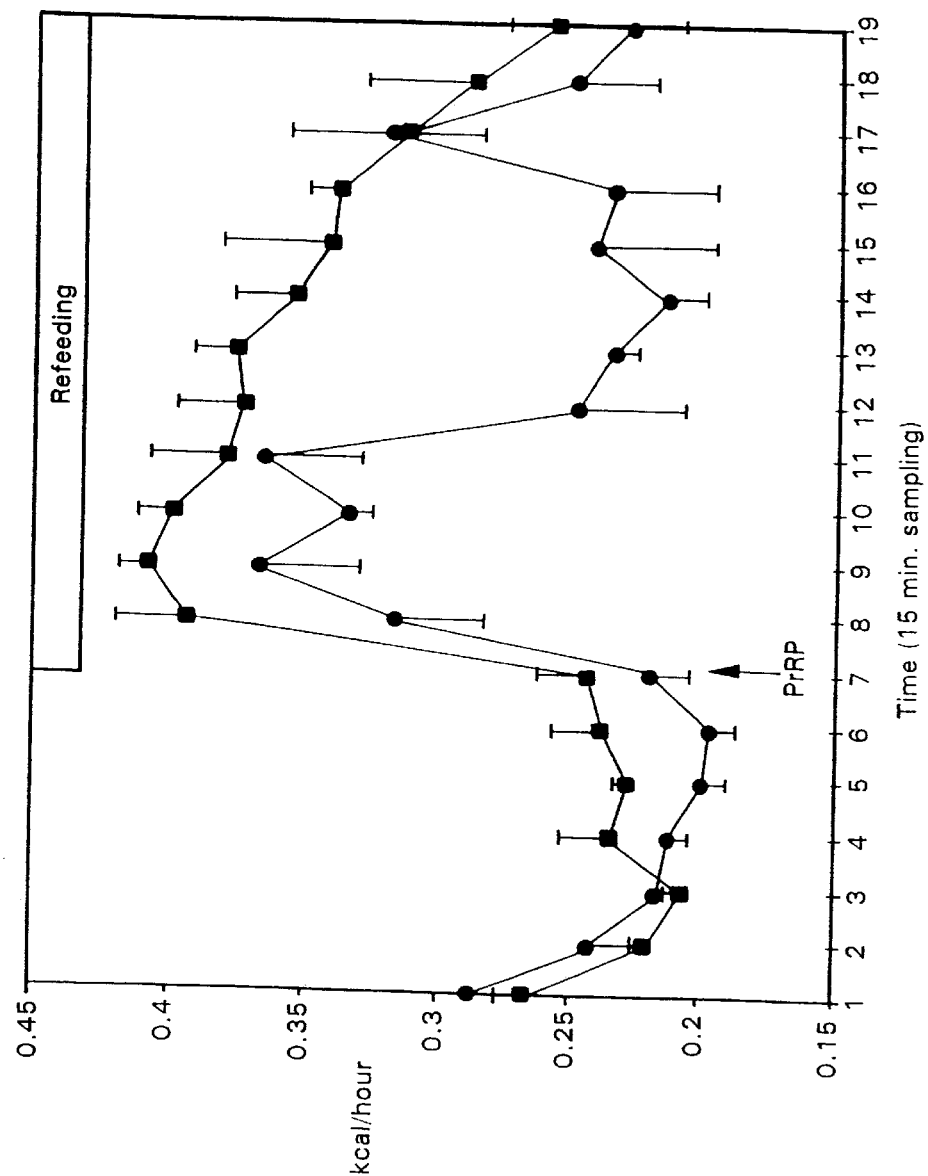
FIG. 7 is a graph illustrating the results of an experiment examining the effect of PrRP on the metabolic rate of lean male mice permitted access to food.

These experiments demonstrated that PrRP increases the metabolic rate of lean male mice having no access to food (FIG. 6; closed squares=PrRP treatment; closed diamonds=control). This increase in metabolic rate may be associated with an increase in food seeking behavior. These experiments also demonstrated the PrRP increases the metabolic rate of lean mice having access to food (FIG. 7 closed squares=PrRP treatment; closed diamonds=control). This increase in metabolic rate suggests that PrRP increases metabolic rate independently of its stimulatory effect on food seeking behavior.

Example 4

Isolation of a cDNA Encoding Murine GPR10

The cDNA sequence of murine GPR10 (also referred to as 101) is depicted in FIG. 1. The predicted amino acid sequence of murine GPR10 is depicted in FIG. 2. A clone encoding human GPR10 was identified as follows. A pair of degenerate probes designed to recognize conserved regions within G protein-coupled receptors and RT-PCR was used to amplify sequences which potentially encode a protein related to a G coupled protein receptor. Sequencing of the clones so identified led to the identification of a clone encoding a protein, murine GPR10 (also referred to as 101) with a high degree of similarity to human GPR10. FIG. 8 depicts an alignment of human GPR10 with hGR3 (human), UHR1 (rat), and murine GPR10.

Example 5

Signal Transduction Assays

The activity of murine GPR10 or a homologue thereof, e.g., human GPR10 (Accession No. P49683), rat UHR-1 (Accession No. Q64121), human hGR3, or murine GPR10 can be measured using any assay suitable for the measurement of the activity of a G protein-coupled receptor. Signal transduction activity of a G protein-coupled receptor can be monitor by monitoring intracellular $Ca^{2+}$, cAMP, inosital 1,4,5-trisphophate ($IP_3$), or 1,2-diacylglycerol (DAG) Assays for the measurement of intracellular $Ca^{2+}$ are described in Sakurai et al. (EP 480 381). Intracellular $IP_3$ can be measured using a kit available from Amersham, Inc. (Arlington Heights, Ill.). A kit for measuring intracellular cAMP is available from Diagnostic Products, Inc. (Los Angeles, Calif.).

Activation of a G protein-coupled receptor triggers the release of $Ca^{2+}$ ions sequestered in the mitochondria, endoplasmic reticulum, and other cytoplasmic vesicles into the cytoplasm. Fluorescent dyes, e.g., fura-2, can be used to measure the concentration of free cytoplasmic $Ca^{2+}$. The ester of fura-2, which is lipophilic and can diffuse across the cell membrane, is added to the media of the host cells expressing GPR10. Once inside the cell, the fura-2 ester is hydrolyzed by cytosolic esterases to its non-lipophilic form, and then the dye cannot diffuse back out of the cell. The non-lipophilic form of fura-2 will fluoresce when it binds to free $Ca^{2+}$. The fluorescence can be measured without lysing the cells at an excitation spectrum of 340 nm or 380 nm and at fluorescence spectrum of 500 nm (Sakurai et al., EP 480 381).

Upon activation of a G protein-coupled receptor, the rise of free cytosolic $Ca^{2+}$, concentrations is preceded by the hydrolysis of phosphatidylinositol 4,5-bisphosphate. Hydrolysis of this phospholipid by the phospholipase C yields 1,2-diacylglycerol (DAG), which remains in the membrane, and water-soluble inosital 1,4,5-trisphophate ($IP_3$). Binding of ligand or agonists will increase the concentration of DAG and $IP_3$. Thus, signal transduction activity can be measured by monitoring the concentration of these hydrolysis products.

To measure the $IP_3$ concentrations, radioactivity labeled $^3H$-inositol is added to the media of host cells expressing GPR10. The $^3H$-inositol is taken up by the cells and incorporated into $IP_3$. The resulting inositol triphosphate is separated from the mono and di-phosphate forms and measured (Sakurai et al., EP 480 381). Alternatively, Amersham provides an inosital 1,4,5-triphosphate assay system. With this system Amersham provides tritylated inositol 1,4,5-triphosphate and a receptor capable of distinguishing the radioactive inositol from other inositol phosphates. With these reagents an effective and accurate competition assay can be performed to determine the inositol triphosphate levels.

Cyclic AMP levels can be measured according to the methods described in Gilman et al., *Proc. Natl. Acad. Sci* 67:305–312 (1970). In addition, a kit for assaying levels of cAMP is available from Diagnostic Products Corp. (Los Angeles, Calif.).

What is claimed is:

1. A method for identifying candidate compounds useful for modulating body weight, feeding behavior or metabolic rate, the method comprising:
   a) contacting a test compound with a mammalian GPR10; and
   b) determining whether the test compound modulates the binding of PrRP to the mammalian GPR10,
      thereby identifiying the test compound as a candidate compound useful for modulating body weight, feeding behavior or metabolic rate if the test compound modulates the binding PrRP to the mammalian GPR10.

2. A method for identifying candidate compounds useful for modulatin body weight, feeding behavior or metabolic rate, comprising the steps of the method of claim 1, and further comprising:
   d) administering a compound which modulates the binding of PrRp to the mammalian GPR10 in step (b) to a mammal; and
   e) determining whether the compound modulates body weight, feeding behavior, or metabolic rate of the mammal,
      thereby identifying the test compound as a candidate compound useful for modulating body weight, feeding behavior or metabolic rate if the test compound modulates body weight, feeding behavior, or metabolic rate of the mammal.

3. The method of claim 1, wherein the mammalian GPR10 is expressed on the surface of a recombinant cell.

4. The method of claim 1, wherein the recombinant cell is an eukaryotic cell.

5. A method for identifying candidate compounds useful for modulating body weight, feeding behavior or metabolic rate, the method comprising:
   a) contacting a test compound with a mammalian GPR10;
   b) determining whether the test compound modulates the activity of the mammalian GPR10; and
   c) identifying the test compound as a candidate compound useful for modulating body weight, feeding behavior or metabolic rate if the test compound modulates the activity of the mammalian GPR10.

6. A method for identifying candidate compounds useful for modulating body weight, feeding behavior or metabolic rate, comprising the steps of the method of claim 5, and further comprising:
   d) administering a compound identified as a candidate compound for modulating body weight, feeding behavior or metabolic rate in step (b) to a mammal; and
   e) determining whether the compound modulates body weight, feeding behavior, or metabolic rate of the mammal,
      thereby identifying the test compound as a candidate compound useful for modulating body weight, feeding behavior or metabolic rate if the test compound modulates the body weight, feeding behavior or metabolic rate of the mammal.

7. The method of claim 5 wherein the activity of mammalian GPR10 is determined by measuring the level of cAMP in the cell.

8. The method of claim 5 wherein the activity of the mammalian GPR10 is determined by measuring the level of cytoplasmic $Ca^{2+}$ in the cell.

9. The method of claim 7 wherein which the cell further contains a reporter gene operatively associated with a cAMP responsive element, and the level of cAMP is measured by measuring expression of the reporter gene.

10. The method of claim 9 in which the reporter gene selected from the group consisting of alkaline phosphatase, chloramphenicol acetyltransferase, luciferase, glucuronide synthetase, growth hormone, and placental alkaline phosphatase.

11. The method of claim 5 wherein the activity of the mammalian GPR10 is measured by measuring intracellular inositol 1,4,5-trisphophate (IP3).

12. The method of claim 5 wherein the activity of the mammalian GPR10 is measured by measuring intracellular 1,2-diacylglycerol (DAG).

13. The method of claim 2 or claim 6, wherein the mammal is a mouse.

14. The method of claim 13, wherein the mouse is an ob/ob mouse.

15. The method of claim 1 or claim 5 wherein the mammalian GPR10 is murine GPR10.

16. The method of claim 1 or claim 5 wherein the mammalian GPR10 is human GPR10.

* * * * *

SEQUENCE LISTING

```
<160> NUMBER OF SEQ ID NOS: 7

<210> SEQ ID NO 1
<211> LENGTH: 1113
<212> TYPE: DNA
<213> ORGANISM: Mus musculus
<220> FEATURE:
<221> NAME/KEY: CDS
<222> LOCATION: (1)...(1110)

<400> SEQUENCE: 1 atg acc tca ctg tcc act gag acc act gga gac ccc gat ttg tct tct       48
Met Thr Ser Leu Ser Thr Glu Thr Thr Gly Asp Pro Asp Leu Ser Ser
  1               5                  10                  15 ggg ctg ttg cca gcc agc tcc act cca gcc aac cag agc gca gag gcc       96
Gly Leu Leu Pro Ala Ser Ser Thr Pro Ala Asn Gln Ser Ala Glu Ala
             20                  25                  30 tcg gag ggc aac ctg tct gcg acg gtt ccc cga gct gca gca gtc acg      144
```

```
Ser Glu Gly Asn Leu Ser Ala Thr Val Pro Arg Ala Ala Val Thr
         35                  40                  45 ccg ttc cag agc ctg cag ctg gtg cac cag ctg aag ggg ttg atc gtg      192
Pro Phe Gln Ser Leu Gln Leu Val His Gln Leu Lys Gly Leu Ile Val
 50                  55                  60 atg ctg tac agc att gtg gtg gtc gtg ggt ctg gtg ggc aac tgc ctg      240
Met Leu Tyr Ser Ile Val Val Val Val Gly Leu Val Gly Asn Cys Leu
 65                  70                  75                  80 ctt gtg ctg gtg atc gcg cgc gtg cgc cgg ctg cac aac gtg acc aac      288
Leu Val Leu Val Ile Ala Arg Val Arg Arg Leu His Asn Val Thr Asn
                 85                  90                  95 ttc ctc att ggc aac ctg gcc ttg tcc gac gtg ctc atg tgt gcc gcc      336
Phe Leu Ile Gly Asn Leu Ala Leu Ser Asp Val Leu Met Cys Ala Ala
            100                 105                 110 tgt gtg cct ctc acg ctg gct tat gcc ttt gaa cct cgg ggc tgg gtg      384
Cys Val Pro Leu Thr Leu Ala Tyr Ala Phe Glu Pro Arg Gly Trp Val
        115                 120                 125 ttc ggt gga ggc ctg tgt cat ctg gtt ttc ttc ctg cag ccg gtc acc      432
Phe Gly Gly Gly Leu Cys His Leu Val Phe Phe Leu Gln Pro Val Thr
    130                 135                 140 gtc tat gta tcg gtg ttc aca ctc acc aca atc gcc ttg gac cgc tat      480
Val Tyr Val Ser Val Phe Thr Leu Thr Thr Ile Ala Leu Asp Arg Tyr
145                 150                 155                 160 gtg gtt ctg gtg cac ccg cta cgt cgg cgc att tca ctg agg ctc agc      528
Val Val Leu Val His Pro Leu Arg Arg Arg Ile Ser Leu Arg Leu Ser
                165                 170                 175 gcc tac gcg gtg ctg ggc atc tgg gct cta tct gca gtg ctg gcg ctg      576
Ala Tyr Ala Val Leu Gly Ile Trp Ala Leu Ser Ala Val Leu Ala Leu
            180                 185                 190 ccg gcc gcg gtg cac acc tac cat gtg gag ctc aag ccc cac gac gtg      624
Pro Ala Ala Val His Thr Tyr His Val Glu Leu Lys Pro His Asp Val
        195                 200                 205 cgc ctc tgc gag gag ttc tgg ggc tcg cag gag cgc caa cgc cag atc      672
Arg Leu Cys Glu Glu Phe Trp Gly Ser Gln Glu Arg Gln Arg Gln Ile
    210                 215                 220 tac gcc tgg ggg ctg ctt ctg ggc acc tat ttg ctc ccc ctg ctg gcc      720
Tyr Ala Trp Gly Leu Leu Leu Gly Thr Tyr Leu Leu Pro Leu Leu Ala
225                 230                 235                 240 atc ctc ctg tct tac gta cgg gtg tca gtg aag ctg agg aac cgc gtg      768
Ile Leu Leu Ser Tyr Val Arg Val Ser Val Lys Leu Arg Asn Arg Val
                245                 250                 255 gtg cct ggc agc gtg acc cag agt caa gct gac tgg gac cga gcg cgt      816
Val Pro Gly Ser Val Thr Gln Ser Gln Ala Asp Trp Asp Arg Ala Arg
            260                 265                 270 cgc cgc cgc act ttc tgt ctg ctg gtg gtg gtg gta gtg ttc gcg           864
Arg Arg Arg Thr Phe Cys Leu Leu Val Val Val Val Val Phe Ala
        275                 280                 285 gtc tgc tgg ctg ccg ctg cac att ttc aac cta ttg cga gac ctg gac      912
Val Cys Trp Leu Pro Leu His Ile Phe Asn Leu Leu Arg Asp Leu Asp
    290                 295                 300 ccg cgt gcc atc gac ccc tac gcc ttc ggg ctg gtg cag cta ctc tgc      960
Pro Arg Ala Ile Asp Pro Tyr Ala Phe Gly Leu Val Gln Leu Leu Cys
305                 310                 315                 320 cac tgg ctt gct atg agc tcc gcc tgc tac aac ccc ttc atc tat gca     1008
His Trp Leu Ala Met Ser Ser Ala Cys Tyr Asn Pro Phe Ile Tyr Ala
                325                 330                 335 tgg ctg cac gac agc ttt cga gag gag ctg cgc aag atg ctg ctg tcc     1056
Trp Leu His Asp Ser Phe Arg Glu Glu Leu Arg Lys Met Leu Leu Ser
            340                 345                 350
```

```
tgg ccc cgc aag att gtg cct cat ggc cag aac atg acc gtc agc gtg    1104
Trp Pro Arg Lys Ile Val Pro His Gly Gln Asn Met Thr Val Ser Val
        355                 360                 365 gtc atc tga                                                        1113
Val Ile
    370

<210> SEQ ID NO 2
<211> LENGTH: 370
<212> TYPE: PRT
<213> ORGANISM: Mus musculus

<400> SEQUENCE: 2

Met Thr Ser Leu Ser Thr Glu Thr Thr Gly Asp Pro Asp Leu Ser Ser
 1               5                  10                  15

Gly Leu Leu Pro Ala Ser Ser Thr Pro Ala Asn Gln Ser Ala Glu Ala
                20                  25                  30

Ser Glu Gly Asn Leu Ser Ala Thr Val Pro Arg Ala Ala Ala Val Thr
            35                  40                  45

Pro Phe Gln Ser Leu Gln Leu Val His Gln Leu Lys Gly Leu Ile Val
        50                  55                  60

Met Leu Tyr Ser Ile Val Val Val Gly Leu Val Gly Asn Cys Leu
 65                  70                  75                  80

Leu Val Leu Val Ile Ala Arg Val Arg Arg Leu His Asn Val Thr Asn
                85                  90                  95

Phe Leu Ile Gly Asn Leu Ala Leu Ser Asp Val Leu Met Cys Ala Ala
            100                 105                 110

Cys Val Pro Leu Thr Leu Ala Tyr Ala Phe Glu Pro Arg Gly Trp Val
        115                 120                 125

Phe Gly Gly Gly Leu Cys His Leu Val Phe Phe Leu Gln Pro Val Thr
130                 135                 140

Val Tyr Val Ser Val Phe Thr Leu Thr Thr Ile Ala Leu Asp Arg Tyr
145                 150                 155                 160

Val Val Leu Val His Pro Leu Arg Arg Arg Ile Ser Leu Arg Leu Ser
                165                 170                 175

Ala Tyr Ala Val Leu Gly Ile Trp Ala Leu Ser Ala Val Leu Ala Leu
            180                 185                 190

Pro Ala Ala Val His Thr Tyr His Val Glu Leu Lys Pro His Asp Val
        195                 200                 205

Arg Leu Cys Glu Glu Phe Trp Gly Ser Gln Glu Arg Gln Arg Gln Ile
    210                 215                 220

Tyr Ala Trp Gly Leu Leu Leu Gly Thr Tyr Leu Leu Pro Leu Leu Ala
225                 230                 235                 240

Ile Leu Leu Ser Tyr Val Arg Val Ser Val Lys Leu Arg Asn Arg Val
                245                 250                 255

Val Pro Gly Ser Val Thr Gln Ser Gln Ala Asp Trp Asp Arg Ala Arg
            260                 265                 270

Arg Arg Arg Thr Phe Cys Leu Leu Val Val Val Val Val Phe Ala
        275                 280                 285

Val Cys Trp Leu Pro Leu His Ile Phe Asn Leu Leu Arg Asp Leu Asp
    290                 295                 300

Pro Arg Ala Ile Asp Pro Tyr Ala Phe Gly Leu Val Gln Leu Leu Cys
305                 310                 315                 320

His Trp Leu Ala Met Ser Ser Ala Cys Tyr Asn Pro Phe Ile Tyr Ala
                325                 330                 335
```

```
Trp Leu His Asp Ser Phe Arg Glu Glu Leu Arg Lys Met Leu Leu Ser
            340                 345                 350

Trp Pro Arg Lys Ile Val Pro His Gly Gln Asn Met Thr Val Ser Val
            355                 360                 365

Val Ile
    370

<210> SEQ ID NO 3
<211> LENGTH: 370
<212> TYPE: PRT
<213> ORGANISM: Mus musculus

<400> SEQUENCE: 3

Met Thr Ser Leu Ser Thr Glu Thr Thr Gly Asp Pro Asp Leu Ser Ser
 1               5                  10                  15

Gly Leu Leu Pro Ala Ser Ser Thr Pro Ala Asn Gln Ser Ala Glu Ala
            20                  25                  30

Ser Glu Gly Asn Leu Ser Ala Thr Val Pro Arg Ala Ala Ala Val Thr
        35                  40                  45

Pro Phe Gln Ser Leu Gln Leu Val His Gln Leu Lys Gly Leu Ile Val
    50                  55                  60

Met Leu Tyr Ser Ile Val Val Val Gly Leu Val Gly Asn Cys Leu
 65                  70                  75                  80

Leu Val Leu Val Ile Ala Arg Val Arg Arg Leu His Asn Val Thr Asn
                85                  90                  95

Phe Leu Ile Gly Asn Leu Ala Leu Ser Asp Val Leu Met Cys Ala Ala
            100                 105                 110

Cys Val Pro Leu Thr Leu Ala Tyr Ala Phe Glu Pro Arg Gly Trp Val
        115                 120                 125

Phe Gly Gly Gly Leu Cys His Leu Val Phe Phe Leu Gln Pro Val Thr
    130                 135                 140

Val Tyr Val Ser Val Phe Thr Leu Thr Thr Ile Ala Leu Asp Arg Tyr
145                 150                 155                 160

Val Val Leu Val His Pro Leu Arg Arg Arg Ile Ser Leu Arg Leu Ser
                165                 170                 175

Ala Tyr Ala Val Leu Gly Ile Trp Ala Leu Ser Ala Val Leu Ala Leu
            180                 185                 190

Pro Ala Ala Val His Thr Tyr His Val Glu Leu Lys Pro His Asp Val
        195                 200                 205

Arg Leu Cys Glu Glu Phe Trp Gly Ser Gln Glu Arg Gln Arg Gln Ile
    210                 215                 220

Tyr Ala Trp Gly Leu Leu Leu Gly Thr Tyr Leu Leu Pro Leu Leu Ala
225                 230                 235                 240

Ile Leu Leu Ser Tyr Val Arg Val Ser Val Lys Leu Arg Asn Arg Val
                245                 250                 255

Val Pro Gly Ser Val Thr Gln Ser Gln Ala Asp Trp Asp Arg Ala Arg
            260                 265                 270

Arg Arg Arg Thr Phe Cys Leu Leu Val Val Val Val Val Phe Ala
        275                 280                 285

Val Cys Trp Leu Pro Leu His Ile Phe Asn Leu Leu Arg Asp Leu Asp
    290                 295                 300

Pro Arg Ala Ile Asp Pro Tyr Ala Phe Gly Leu Val Gln Leu Leu Cys
305                 310                 315                 320

His Trp Leu Ala Met Ser Ser Ala Cys Tyr Asn Pro Phe Ile Tyr Ala
                325                 330                 335
```

```
Trp Leu His Asp Ser Phe Arg Glu Glu Leu Arg Lys Met Leu Leu Ser
            340                 345                 350

Trp Pro Arg Lys Ile Val Pro His Gly Gln Asn Met Thr Val Ser Val
            355                 360                 365

Val Ile
    370

<210> SEQ ID NO 4
<211> LENGTH: 31
<212> TYPE: PRT
<213> ORGANISM: Mus musculus

<400> SEQUENCE: 4

Ser Arg Ala His Gln His Ser Met Glu Thr Arg Thr Pro Asp Ile Asn
 1               5                  10                  15

Pro Ala Trp Tyr Thr Gly Arg Gly Ile Arg Pro Val Gly Arg Phe
                20                  25                  30

<210> SEQ ID NO 5
<211> LENGTH: 370
<212> TYPE: PRT
<213> ORGANISM: Homo sapiens

<400> SEQUENCE: 5

Met Ala Ser Ser Thr Thr Arg Gly Pro Arg Val Ser Asp Leu Phe Ser
 1               5                  10                  15

Gly Leu Pro Pro Ala Val Thr Thr Pro Ala Asn Gln Ser Ala Glu Ala
                20                  25                  30

Ser Ala Gly Asn Gly Ser Val Ala Gly Ala Asp Ala Pro Ala Val Thr
            35                  40                  45

Pro Phe Gln Ser Leu Gln Leu Val His Gln Leu Lys Gly Leu Ile Val
    50                  55                  60

Leu Leu Tyr Ser Val Val Val Val Gly Leu Val Gly Asn Cys Leu
65                  70                  75                  80

Leu Val Leu Val Ile Ala Arg Val Arg Arg Leu His Asn Val Thr Asn
                85                  90                  95

Phe Leu Ile Gly Asn Leu Ala Leu Ser Asp Val Leu Met Cys Thr Ala
            100                 105                 110

Cys Val Pro Leu Thr Leu Ala Tyr Ala Phe Glu Pro Arg Gly Trp Val
        115                 120                 125

Phe Gly Gly Gly Leu Cys His Leu Val Phe Phe Leu Gln Pro Val Thr
    130                 135                 140

Val Tyr Val Ser Val Phe Thr Leu Thr Thr Ile Ala Val Asp Arg Tyr
145                 150                 155                 160

Val Val Leu Val His Pro Leu Arg Arg Arg Ile Ser Leu Arg Leu Ser
                165                 170                 175

Ala Tyr Ala Val Leu Ala Ile Trp Ala Leu Ser Ala Val Leu Ala Leu
            180                 185                 190

Pro Ala Ala Val His Thr Tyr His Val Glu Leu Lys Pro His Asp Val
        195                 200                 205

Arg Leu Cys Glu Glu Phe Trp Gly Ser Gln Glu Arg Gln Arg Gln Leu
    210                 215                 220

Tyr Ala Trp Gly Leu Leu Leu Val Thr Tyr Leu Leu Pro Leu Leu Val
225                 230                 235                 240

Ile Leu Leu Ser Tyr Val Arg Val Ser Val Lys Leu Arg Asn Arg Val
                245                 250                 255
```

Val Pro Gly Cys Val Thr Gln Ser Gln Ala Asp Trp Asp Arg Ala Arg
                260                 265                 270

Arg Arg Arg Thr Phe Cys Leu Leu Val Val Val Val Val Phe Ala
            275                 280                 285

Val Cys Trp Leu Pro Leu His Val Phe Asn Leu Leu Arg Asp Leu Asp
    290                 295                 300

Pro His Ala Ile Asp Pro Tyr Ala Phe Gly Leu Val Gln Leu Leu Cys
305                 310                 315                 320

His Trp Leu Ala Met Ser Ser Ala Cys Tyr Asn Pro Phe Ile Tyr Ala
                325                 330                 335

Trp Leu His Asp Ser Phe Arg Glu Glu Leu Arg Lys Leu Leu Val Ala
                340                 345                 350

Trp Pro Arg Lys Ile Ala Pro His Gly Gln Asn Met Thr Val Ser Val
            355                 360                 365

Val Ile
    370

<210> SEQ ID NO 6
<211> LENGTH: 369
<212> TYPE: PRT
<213> ORGANISM: Homo sapiens

<400> SEQUENCE: 6

Met Ala Ser Ser Thr Thr Arg Gly Pro Arg Val Ser Asp Leu Phe Ser
1               5                   10                  15

Gly Leu Pro Pro Ala Val Thr Thr Pro Ala Asn Gln Ser Ala Glu Ala
                20                  25                  30

Ser Ala Gly Asn Gly Ser Val Ala Gly Ala Asp Ala Pro Ala Val Thr
            35                  40                  45

Pro Phe Gln Ser Leu Gln Leu Val His Gln Leu Lys Gly Leu Ile Val
        50                  55                  60

Leu Leu Tyr Ser Val Val Val Val Gly Leu Val Gly Asn Cys Leu
65                  70                  75                  80

Leu Val Leu Val Ile Ala Arg Val Pro Arg Leu His Asn Val Thr Asn
                85                  90                  95

Phe Leu Ile Gly Asn Leu Ala Leu Ser Asp Val Leu Met Cys Thr Ala
                100                 105                 110

Cys Val Pro Leu Thr Leu Ala Tyr Ala Phe Glu Pro Arg Gly Trp Val
            115                 120                 125

Phe Gly Gly Gly Leu Cys His Leu Val Phe Phe Leu Gln Pro Val Thr
    130                 135                 140

Val Tyr Val Ser Val Phe Thr Leu Thr Thr Ile Ala Val Asp Arg Tyr
145                 150                 155                 160

Val Val Leu Val His Pro Leu Arg Arg Ala Ser Arg Cys Ala Ser Ala
                165                 170                 175

Tyr Ala Val Leu Ala Ile Trp Ala Leu Ser Ala Val Leu Ala Leu Pro
                180                 185                 190

Pro Ala Val His Thr Tyr His Val Glu Leu Lys Pro His Asp Val Arg
            195                 200                 205

Leu Cys Glu Glu Phe Trp Gly Ser Gln Glu Arg Gln Arg Gln Leu Tyr
        210                 215                 220

Ala Trp Gly Leu Leu Leu Val Thr Tyr Leu Leu Pro Leu Leu Val Ile
225                 230                 235                 240

Leu Leu Ser Tyr Val Arg Val Ser Val Lys Leu Arg Asn Arg Val Val

-continued

```
                245                 250                 255
Pro Gly Cys Val Thr Gln Ser Gln Ala Asp Trp Asp Arg Ala Arg Arg
            260                 265                 270

Arg Arg Thr Phe Cys Leu Leu Val Val Val Val Val Phe Ala Val
        275                 280                 285

Cys Trp Leu Pro Leu His Val Phe Asn Leu Leu Arg Asp Leu Asp Pro
290                 295                 300

His Ala Ile Asp Pro Tyr Ala Phe Gly Leu Val Gln Leu Leu Cys His
305                 310                 315                 320

Trp Leu Ala Met Ser Ser Ala Cys Tyr Asn Pro Phe Ile Tyr Ala Trp
                325                 330                 335

Leu His Asp Ser Phe Arg Glu Glu Leu Arg Lys Leu Leu Val Ala Trp
            340                 345                 350

Pro Arg Lys Ile Ala Pro His Gly Gln Asn Met Thr Val Ser Val Val
        355                 360                 365

Ile

<210> SEQ ID NO 7
<211> LENGTH: 370
<212> TYPE: PRT
<213> ORGANISM: Mus musculus

<400> SEQUENCE: 7

Met Thr Ser Leu Pro Pro Gly Thr Thr Gly Asp Pro Asp Leu Phe Ser
1               5                  10                  15

Gly Pro Ser Pro Ala Gly Ser Thr Pro Ala Asn Gln Ser Ala Glu Ala
            20                  25                  30

Ser Glu Ser Asn Val Ser Ala Thr Val Pro Arg Ala Ala Ala Val Thr
        35                  40                  45

Pro Phe Gln Ser Leu Gln Leu Val His Gln Leu Lys Gly Leu Ile Val
    50                  55                  60

Met Leu Tyr Ser Ile Val Val Val Gly Leu Val Gly Asn Cys Leu
65                  70                  75                  80

Leu Val Leu Val Ile Ala Arg Val Arg Arg Leu His Asn Val Thr Asn
                85                  90                  95

Phe Leu Ile Gly Asn Leu Ala Leu Ser Asp Val Leu Met Cys Ala Ala
            100                 105                 110

Cys Val Pro Leu Thr Leu Ala Tyr Ala Phe Glu Pro Arg Gly Trp Val
        115                 120                 125

Phe Gly Gly Gly Leu Cys His Leu Val Phe Phe Leu Gln Pro Val Thr
    130                 135                 140

Val Tyr Val Ser Val Phe Thr Leu Thr Thr Ile Ala Val Asp Arg Tyr
145                 150                 155                 160

Val Val Leu Val His Pro Leu Arg Arg Arg Ile Ser Leu Lys Leu Ser
                165                 170                 175

Ala Tyr Ala Val Leu Gly Ile Trp Ala Leu Ser Ala Val Leu Ala Leu
            180                 185                 190

Pro Ala Ala Val His Thr Tyr His Val Glu Leu Lys Pro His Asp Val
        195                 200                 205

Arg Leu Cys Glu Glu Phe Trp Gly Ser Gln Glu Arg Gln Arg Gln Ile
    210                 215                 220

Tyr Ala Trp Gly Leu Leu Leu Gly Thr Tyr Leu Leu Pro Leu Leu Ala
225                 230                 235                 240

Ile Leu Leu Ser Tyr Val Arg Val Ser Val Lys Leu Arg Asn Arg Val
```

-continued

```
                        245                 250                 255
Val Pro Gly Ser Val Thr Gln Ser Gln Ala Asp Trp Asp Arg Ala Arg
            260                 265                 270

Arg Arg Arg Thr Phe Cys Leu Leu Val Val Val Val Val Phe Ala
            275                 280                 285

Leu Cys Trp Leu Pro Leu His Ile Phe Asn Leu Leu Arg Asp Leu Asp
    290                 295                 300

Pro Arg Ala Ile Asp Pro Tyr Ala Phe Gly Leu Val Gln Leu Leu Cys
305                 310                 315                 320

His Trp Leu Ala Met Ser Ser Ala Cys Tyr Asn Pro Phe Ile Tyr Ala
                325                 330                 335

Trp Leu His Asp Ser Phe Arg Glu Glu Leu Arg Lys Met Leu Leu Ser
            340                 345                 350

Trp Pro Arg Lys Ile Val Pro His Gly Gln Asn Met Thr Val Ser Val
        355                 360                 365

Val Ile
    370
```